US011839634B2

(12) United States Patent
Guglielmetti et al.

(10) Patent No.: US 11,839,634 B2
(45) Date of Patent: *Dec. 12, 2023

(54) USE OF A COMPOSITION COMPRISING MICROORGANISMS TO INCREASE THE INTESTINAL PRODUCTION OF BUTYRIC ACID, FOLIC ACID OR NIACIN AND/OR DECREASE THE INTESTINAL PRODUCTION OF SUCCINIC ACID

(71) Applicant: ALFASIGMA S.P.A., BOLOGNA (IT)

(72) Inventors: Simone Domenico Guglielmetti, Milan (IT); Ruggero Rossi, Milan (IT); Walter Fiore, Trezzano Rosa (IT); Andrea Biffi, Urgnano (IT)

(73) Assignee: ALFASIGMA S.P.A., Bologna (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/916,961

(22) PCT Filed: Sep. 5, 2014

(86) PCT No.: PCT/IB2014/064285
§ 371 (c)(1),
(2) Date: Mar. 4, 2016

(87) PCT Pub. No.: WO2015/033305
PCT Pub. Date: Mar. 12, 2015

(65) Prior Publication Data
US 2016/0296569 A1  Oct. 13, 2016

(30) Foreign Application Priority Data
Sep. 6, 2013  (IT) .................. MI2013A001467

(51) Int. Cl.
*A61K 35/747* (2015.01)
*A23L 33/135* (2016.01)
*A23L 33/21* (2016.01)
*A61P 1/00* (2006.01)
*A61K 9/00* (2006.01)
*A61K 9/48* (2006.01)
*A61K 35/00* (2006.01)

(52) U.S. Cl.
CPC .......... *A61K 35/747* (2013.01); *A23L 33/135* (2016.08); *A23L 33/21* (2016.08); *A61K 9/0053* (2013.01); *A61K 9/48* (2013.01); *A61P 1/00* (2018.01); *A23V 2002/00* (2013.01); *A23Y 2220/63* (2013.01); *A61K 2035/11* (2013.01)

(58) Field of Classification Search
CPC .......... A23V 2002/00; A23V 2200/32; A23V 2200/3202; A23V 2200/3204; A23L 33/135; A23L 33/21; A23Y 2220/63; A61K 2035/11; A61K 35/747; A61K 9/0053; A61K 9/48; A61P 1/00
See application file for complete search history.

(56) References Cited

U.S. PATENT DOCUMENTS

| 5,531,989 | A | 7/1996 | Paul |
| 5,716,615 | A | 2/1998 | Cavaliere Vesely et al. |
| 6,770,246 | B1 | 8/2004 | Husek |
| 7,510,734 | B2 | 3/2009 | Sullivan et al. |
| 11,400,124 | B2 | 8/2022 | Biffi |
| 11,464,814 | B2 | 10/2022 | Biffi |
| 11,591,416 | B2 | 2/2023 | Biffi et al. |
| 2002/0090416 | A1 | 7/2002 | Connolly |
| 2003/0031659 | A1 | 2/2003 | Farmer |
| 2003/0092163 | A1 | 5/2003 | Collins et al. |
| 2003/0157146 | A1* | 8/2003 | Rautonen ................. A61P 37/00 424/442 |
| 2003/0190369 | A1* | 10/2003 | Lovett ..................... A61K 33/42 424/602 |
| 2004/0170617 | A1 | 9/2004 | Finegold |
| 2005/0196480 | A1 | 9/2005 | Sullivan et al. |
| 2006/0057704 | A1 | 3/2006 | Schlothauer et al. |
| 2006/0067921 | A1 | 3/2006 | Conway |
| 2008/0081035 | A1* | 4/2008 | Parmely ................... C12N 9/62 424/94.63 |
| 2008/0193603 | A1* | 8/2008 | Hayes .................... A61K 36/48 426/74 |
| 2008/0241226 | A1 | 10/2008 | Abeln et al. |
| 2009/0061446 | A1 | 3/2009 | Nimi et al. |

(Continued)

FOREIGN PATENT DOCUMENTS

| CN | 1161795 A | 10/1997 |
| CN | 1701116 A | 11/2005 |

(Continued)

OTHER PUBLICATIONS

European Food Safety Authority EFSA Journal (2012) 10(6): 2723.*
D'Inca et al. Dig. Dis. Sci. (2011) 56: 1178-1187.*
Ferrario et al. J. Nutrition (published online Sep. 3, 2014) 144: 1787-1796 (Year: 2014).*
Vernia et al. Dig. Disease Sci. (1988) 33(11): 1353-135 (Year: 1988).*
Kay J. Lipid Research (1982) 23: 221-242 (Year: 1982).*
Gould et al. Current Gastroenterology Reports (2009) 11: 354-359; full paper (Year: 2009).*
Leonel et al. Current Opinion in Clinical Nutrition and Metabolic Care (2012), 15(5): 474-479 (Year: 2012).*

(Continued)

Primary Examiner — Allison M Fox
Assistant Examiner — Qing Xu
(74) Attorney, Agent, or Firm — Steinfl + Bruno LLP

(57) ABSTRACT

The present invention relates to the use of a composition comprising bacteria to increase the intestinal production of butyric acid, folic acid or niacin and/or to decrease the intestinal production of succinic acid. Moreover, the present invention relates to the use of said composition for the treatment and/or prevention of an intestinal butyrate- and/or succinate-dependent pathological condition. In particular, for the treatment and/or the prevention of intestinal inflammation, diarrhoea, ulcerative colitis or intestinal colopathies.

10 Claims, 6 Drawing Sheets
Specification includes a Sequence Listing.

(56) References Cited

U.S. PATENT DOCUMENTS

| | | |
|---|---|---|
| 2009/0098088 A1 | 4/2009 | Taylor et al. |
| 2009/0220481 A1 | 9/2009 | Maes et al. |
| 2009/0274662 A1 | 11/2009 | Magowan et al. |
| 2009/0312282 A1 | 12/2009 | Yoshida et al. |
| 2010/0074994 A1 | 3/2010 | Harel et al. |
| 2010/0112564 A1 | 5/2010 | Zhao et al. |
| 2011/0014167 A1* | 1/2011 | Bindels ............ A61K 31/7024 424/93.45 |
| 2011/0038837 A1* | 2/2011 | Nishida ............ A21D 8/045 424/93.3 |
| 2011/0052538 A1 | 3/2011 | Brown et al. |
| 2011/0166100 A1 | 7/2011 | Wu |
| 2011/0305744 A1 | 12/2011 | Russo |
| 2012/0251512 A1 | 10/2012 | Farmer et al. |
| 2012/0269865 A1* | 10/2012 | Roughead ............ A23L 1/308 424/278.1 |
| 2012/0301451 A1 | 11/2012 | Branning et al. |
| 2012/0322773 A1* | 12/2012 | Pravda ............ A61K 31/12 514/166 |
| 2016/0348155 A1 | 12/2016 | Guglielmetti et al. |
| 2017/0035816 A1 | 2/2017 | Biffi |
| 2017/0202231 A1 | 7/2017 | Budelli et al. |
| 2019/0192590 A1 | 6/2019 | Biffi |
| 2019/0290706 A1 | 9/2019 | Biffi et al. |
| 2019/0345268 A1 | 11/2019 | Biffi et al. |
| 2021/0186075 A1 | 6/2021 | Biffi et al. |
| 2021/0236565 A1 | 8/2021 | Biffi |
| 2022/0325234 A1 | 10/2022 | Biffi et al. |
| 2022/0339216 A1 | 10/2022 | Biffi et al. |
| 2022/0354910 A1 | 11/2022 | Biffi et al. |
| 2022/0370520 A1 | 11/2022 | Biffi et al. |
| 2022/0409676 A1 | 12/2022 | Biffi et al. |
| 2023/0052820 A1 | 2/2023 | Biffi |

FOREIGN PATENT DOCUMENTS

| | | |
|---|---|---|
| CN | 1840206 A | 10/2006 |
| CN | 101636173 A | 1/2010 |
| CN | 102919922 A | 2/2013 |
| CN | 103997899 A | 8/2014 |
| CN | 108743851 A | 11/2018 |
| CN | 109310719 A | 2/2019 |
| EP | 1145643 A1 | 10/2001 |
| EP | 2407532 A2 | 1/2012 |
| JP | H0517363 A | 1/1993 |
| JP | 2005-508617 A | 4/2005 |
| JP | 2005-534315 A | 11/2005 |
| JP | 2010-512755 A | 4/2010 |
| JP | 2010161944 A | 7/2010 |
| JP | 2013-515051 A | 5/2013 |
| RU | 2182008 C1 | 5/2002 |
| WO | 00/54788 A1 | 9/2000 |
| WO | 2003/090763 A1 | 11/2003 |
| WO | 2004/022727 A1 | 3/2004 |
| WO | 2005/001109 A2 | 1/2005 |
| WO | 2005/083122 A2 | 9/2005 |
| WO | 2006/050479 A2 | 5/2006 |
| WO | 2007/071815 A1 | 6/2007 |
| WO | 2007/140621 A1 | 12/2007 |
| WO | 2008/119012 A2 | 10/2008 |
| WO | 2008/148798 A2 | 12/2008 |
| WO | 2010/008272 A1 | 1/2010 |
| WO | 2010/008278 A1 | 1/2010 |
| WO | 2010/099824 A1 | 9/2010 |
| WO | 2011/036539 A1 | 3/2011 |
| WO | 2012/154738 A1 | 11/2012 |
| WO | 2014/068338 A1 | 5/2014 |
| WO | 2014/137211 A1 | 9/2014 |
| WO | 2015/000972 A1 | 1/2015 |
| WO | 2015/033304 A1 | 3/2015 |
| WO | 2015/033305 A1 | 3/2015 |
| WO | 2015/162570 A1 | 10/2015 |
| WO | 2015/172191 A1 | 11/2015 |
| WO | 2016/030320 A1 | 3/2016 |
| WO | 2017/195182 A1 | 11/2017 |
| WO | 2017/212433 A1 | 12/2017 |
| WO | 2018/100549 A1 | 6/2018 |
| WO | 2018/109520 A1 | 6/2018 |
| WO | 2018/109730 A1 | 6/2018 |
| WO | 2019/019961 A1 | 1/2019 |
| WO | 2019/053604 A1 | 3/2019 |
| WO | 2019/111189 A1 | 6/2019 |
| WO | 2021/053636 A1 | 3/2021 |
| WO | 2021/053639 A1 | 3/2021 |
| WO | 2021/053641 A2 | 3/2021 |
| WO | 2021/053642 A1 | 3/2021 |
| WO | 2021/090228 A1 | 5/2021 |
| WO | 2021/090228 A4 | 7/2021 |

OTHER PUBLICATIONS

Ferrario et al. J. Nutritional Epidemiology (Sep. 3, 2014) 144: 1787-1796 (Year: 2014).*

Printout of Mayo Clinic, downloaded on Dec. 12, 2022 from https://www.mayoclinic.org/diseases-conditions/diabetic-neuropathy/symptoms-causes/syc-20371580 (Year: 2022).*

Oliveira et al., "Lactobacillus paracasei Reduces Intestinal Inflammation in Adoptive Transfer Mouse Model of Experimental Colitis", Clinical and Developmental Immunology 2011: 1-13 (2011).

Lombardo, "New insights into Lactobacillus and functional intestinal disorders", Minera Gastroenterol. Dietol. 54: 287-293 (2008).

Valerio et al., "Effects of Probiotic Lactobacillus paracasei-enriched Artichokes on Constipated Patients", J Clin Gastroenterol 44: S49-S53 (2010).

Plant et al., "Association of *Lactobacillus* spp. with Peyer's Patches in Mice", Clinical and Diagnostic Laboratory Immunology 8: 320-324 (2001).

Savino et al., "Lactobacillus reuteri DSM 17938 in Infantile Colic: A Randomized, Double-Blind, Placebo-Controlled Trial", Pediatrics 126: e526-e533 (2010).

"Example Cross-Over Study Design (A Phase II, Randomized, Double-Blind Crossover Study of Hypertena and Placebo in Participants with High Blookd Pressure)". ClinicalTrials.gov (2012).

Lombardo, Lucio et al., "Clinical Evaluation of *Lactobacillus paracasei* Subsp. Paracasei F19 with Gluco-Oligosaccharides in the Short-term Treatment of Irritable Bowel Syndrome" Microbial Ecology in Health and Disease 21:28-32 (2009).

LeBlanc et al., "Beneficial effects on host energy metabolism of shot-chain fatty acids and vitamins produced by commensal and probiotic bacteria," Microbial Cell Factories 16:79: 1-10 (2017).

Tursi et al., "Effect of Lactobacillus casei supplementation on the effectiveness and tolerability of a new second-line 10-day quadruple therapy after failure of a first attempt to cure Helicobacter pylori infection," Med Sci Monit 10: CR662-666 (2004).

M. Ausubel, R. Brent, R.E. Kingston, D.D. Moore, J.G. Seidman, J.A. Smith, and K. Struhl. Current protocols in molecular biology, edited vols. 1 and 2. John Wiley & Sons, Inc., Media, PA, 1994.

International Search Report for International Application No. PCT/IB2014/064285 filed on Sep. 5, 2014 on behalf of SOFAR SPA, dated Jan. 29, 2015. 4 pages.

Milani C, Hevia A, Foroni E, et al. Assessing the fecal microbiota: an optimized ion torrent 16S rRNA gene-based analysis protocol. PLoS One. 2013;8(7):e68739, 12 pages. Published Jul. 15, 2013. doi:10.1371/journal.pone.0068739.

Okuda S, Tsuchiya Y, Kiriyama C, Itoh M, Morisaki H. Virtual metagenome reconstruction from 16S rRNA gene sequences. Nat Commun. 2012; 3: 1203).

J.F. Sambrook and D.W. Russell, ed. Molecular Cloning: A Laboratory Manual, 3rd ed., vols. 1,2 and 3Cold Spring Harbor Laboratory Press, 2001, 2100 pp.

Taverniti and Guglielmetti et al., "The immunomodulatory properties of probiotic microorganisms beyond their viability (ghost probiotics: proposal of paraprobiotic concept)" *Department of Food Science and Microbiology (DiSTAM), Universita degli Studi di Milano*,Apr. 16, 2011. 15 pages.

(56) References Cited

OTHER PUBLICATIONS

Written Opinion for International Application No. PCT/IB2014/064285 filed on Sep. 5, 2014 on behalf of SOFAR SPA, dated Jan. 29, 2015. 7 pages.
Aden K. et al., "Metabolic Functions of Gut Microbes Associate with Efficacy of Tumor Necrosis Factor Antagonists in Patients with Inflammatory Bowel Diseases" Gastroenterology, 2019, pp. 1279-1292.
Allegretti J. et al., "Short Chain Fatty Acid Profiles Are Altered by Fecal Microbiota Transplantation for the Treatment of Inflammatory Bowel Disease and Recurrent Clostridioides difficile Infection" *Gastroenterology*,2019, 2 pages.
Balzaretti et al., "A Novel rhamnose-rich heterp-exopolysaccharide isolated from Lactobacillus paracasei DG activates THP-1 human monocytic cells" *University of Huddersfiled Repository Article for Applied and Environmental Microbiology*.Jan. 17, 2017.
Balzaretti et al., "Exploring Lactobacillus paracasei probiosis and metabolic potential", University of Milan PhD thesis, 2015, pp. 1-132.
Balzaretti S. et al., "The vaginal isolate Lactobacillus paracasei LPC-S01 (DSM 26760) is suitable for oral administration" *Frontiers in Microbiology*, vol. 6, Sep. 2015 , 13 pages.
Banasiewicz T. et al., "Determination of butyric acid dosage based on clinical and experimental studies—a literature review" *Gastroenterology Review*,2020, pp. 119-125.
Borren N. et al., "Alterations in Fecal Microbiomes and Serum Metabolomes of Fatigues Patients With Quiescent Inflammatory Bowel Diseases" *Clinical Gastroenterology and Hepatology*, March 2020, 35 pages.
Canadian Office Action for CA Application No. 2,923,392 filed on Sep. 5, 2014 on behalf of SOFAR S.P.A. dated Jun. 1, 2020 4 pages.
Cassard L. et al, "Individual strains of Lactobacillus paracasei differentially inhibit human basophil and mouse mast cell activation," Immunity, Inflammation, and Disease vol. 4, Issue 3., 2016. 11 Pages.
Chassard C. et al., "Functional dysbiosis within the gut microbiota of patients with constipated-irritable bowel syndrome" *Alimentary Pharmacology and Therapeutics*,2012, pp. 828-838.
Chilean Office Action for CL Application No. 201803193 filed on Sep. 5, 2014 dated April 16, 2020 16 pages (English + Original).
Chinese Office Action for CN Application No. 201480049288 filed on Sep. 5, 2014 on behalf of SOFAR S.P.A. dated Sep. 16, 2020 8 pages (English + Original).
Ciucanu I. et al. "A simple and rapid method for the permethylation of carbohydrates" *Carbohydrate Research*,131(1984) pp. 209-217.
Collins M.N. and Birkinshaw C. "Hyaluronic acid based scaffolds for tissue engineering—A review", Carbohydrate Polymers 2013, 1262-1279.
Colombian Office Action for CO Application No. NC2018/0010950 filed on Sep. 5, 2014 on behalf of SOFAR S.P.A. dated Jul. 27, 2020 11 pages (Partial English + Original).
Communication pursuant to Article 94(3) EPC for EP Application No. 147903223 filed on Sep. 5, 2014 on behalf of SOFAR S.P.A. dated Jan. 31, 2020 8 pages.
Compare D. et al., "Lactobacillus casei DG and its postbiotic reduce the inflammatory mucosal response: an eX-vivo organ culture model of post-infectious irritable bowel syndrome" *BMC Gastroenterology*,2017, 8 pages.
Costalos et al., "Enteral feeding of premature infants with *Saccharomyces boulardii*" *Early Human Development*, 74,(2003), 89-96.
Cremon C. et al., "Effect of Lactobacillus paracasei CNCM I-1572 on symptoms, gut microbiota, short chain fatty acids, and immune activation in patients with irritable bowel syndrome: A pilot randomized clinical trial" *UEG Journal*,Sep. 2017, 10 pages.
Crohn's and Colitis Foundation of America. Inflammatory Bowel Disease and Inflammatory Bowel Syndrome: Similarities and Differences. 2014. 12 Pages.
De Souza M.M. et aJ. "Effects of budesonide and probiotics enemas on the systemic inflammatory response of rats with experimental coJitis", Acta Cirurgica Brasileira 2007, 22 (Supp 1. 1 ): 40-45.

Di Mario Francesco et al., "Use of mesalazine in diverticular disease." Journal of Clinical Gastroenterology. vol. 40, Suppl 3, Aug. 2006.
Eurasian Notification of Grant for Application No. 201690464/28 filed on Sep. 5, 2014 on behalf of SOFAR S.P.A. dated Jun. 9, 2020 2 pages (English + Original).
Evans S. "Clinical trial structures" *J EXp Stroke Transl Med*.Mar. 2011, pp. 1-16, 16 pages.
Fakhari A. and Berkland C. "Applications and emerging trends of hyaluronic acid in tissue engineering, as a dermal filler and in osteoarthritis treatment", Acta Biomaterialia 2013, 9, 7081-7092.
Fao and Who et al; "Live microorganisms which, when administered in adequate amounts, confer a health benefit on the host", *World Health Organizations and Food Agriculture Organization*. 2001.
Farup et al., "Probiotics, Symptoms, and Gut Microbiota; What are the relations? A Randomized Controlled Trial in Subjects with Irritable Bowel Syndrome" Gastro Research and Practice, vol. 2012. 7 pages.
Final Office Action for U.S. Appl. No. 14/916,959, filed Mar. 4, 2016 on behalf of SOFAR S.P.A. dated Aug. 21, 2020 48 pages.
Final Office Action for U.S. Appl. No. 14/916,959, filed Mar. 4, 2016 on behalf of SOFAR SPA, dated Jul. 23, 2019. 23 pages.
Final Office Action for U.S. Appl. No. 15/305,470, filed Oct. 20, 2016 on behalf of SOFAR S.P.A. dated Jul. 10, 2020 21 pages.
Final Office Action for U.S. Appl. No. 16/301,361, filed Nov. 13, 2018 on behalf of SOFAR S.P.A. dated Sep. 21, 2020 11 pages.
Final Office Action for U.S. Appl. No. 15/305,470, filed Oct. 20, 2016 on behalf of SOFAR SPA, dated Jan. 14, 2019. 10 pages.
Final Office Action for U.S. Appl. No. 14/916,959, filed Mar. 4, 2016 on behalf of SOFAR SPA, dated Apr. 20, 2018. 26 pages.
Fiorino et al., "P325 Efficacy and Safety of IBD98E, a Sodium Hyaluronate Topical Preparation, in the Induction of Clinical and Endoscopic Remission in Patients with Distal Ulcerative Colitis: An Open Label Study," United European Gastroenterology Journal: 1(1S) (A219).
Floch M.H. et al. "Recommendations for probiotic use—2011 Update", J. Clin.Gastroenterol. 2011, 45: S168-S171.
Food and Agriculture Organization. Health and nutritional properties of probiotics in food including powder milk with live lactic acid bacteria. Oct. 2001: 34 pages.
Gargari G. et al., "Fecal Clostridiales distribution and short-chain fatty acids reflect bowel habits in irritable bowel syndrome" Environmental Microbiology, Sep. 2018, 31 pages.
Gerwig G. et al., "Determination of the absolute configuration of mono-saccharides in complex carbohydrates by capillary G.L.C." *Carbohydrate Research*,77(1979) pp. 1-7.
Gill et al., "Metagenomic Analysis of the Human Distal Gut Microbiome," Science 312: 1355-1359 (2006).
Guglielmetti S. et al., "TgaA, a VirB1-Like Component Belonging to a Putative Type IV Secretion System of Bifidobacterium bifidum MIMBb75" *Applied and Environmental Microbiology*, vol. 80, No. 17,Sep. 2014 pp. 5161-5169.
Gugliemetti et al., "Randomised clinical trial; Bifidobacterium bifidum MIMBb75 significatnly alleviates irritable bowel syndrome and improves quality of life, a double-blind, placebo-controlled study" Alimentary Pharmacology & Therapeutics, p. 1123-1132. 2011.
Guo, Y., et al., "Irritable Bowel Syndrome is Positively Related to Metabolic Syndrome: A Population-Based Cross-Sectional Study," PLoS One. 9(11): e112289. Nov. 10, 2014. 6 pages.
Havea P. "Protein interactions in milk protein concentrate powders" *International Dairy Journal*,vol. 16,2006, pp. 415-422.
Hustoft T. et al., "Effects of varying dietary content of fermentable short-chain carbohydrates on symptoms, fecal microenvironment, and cytokine profiles in patients with irritable bowel syndrome" Neurogastroenterology & Motility, Sep. 2016, 9 pages.
International Search Report for International Application No. PCT/IB2014/064284 filed on Sep. 5, 2014 on behalf of SOFAR SPA, dated Jan. 26, 2015. 6 pages.
International Search Report for International Application No. PCT/IB2017/052850 filed on May 15, 2017 on behalf of SOFAR SPA, dated Aug. 17, 2017. 4 pages.

(56) References Cited

OTHER PUBLICATIONS

International Search Report for International Application No. PCT/IB2017/053389 filed on Jun. 8, 2017 on behalf of SOFAR SPA, dated Oct. 6, 2017. 5 pages.
International Search Report for International Application No. PCT/IB2017/057576 filed on Dec. 1, 2017 on behalf of SOFAR SPA, dated Feb. 22, 2018. 5 pages.
International Search Report for International Application No. PCT/IB2017/057980 filed on Dec. 15, 2017 on behalf of SOFAR SPA, dated Mar. 19, 2018. 4 pages.
International Search report for International Application PCT/IB2015/052938 filed on Apr. 22, 2015 on behalf of SOFAR SPA, dated Jul. 31, 2015. 4 pages.
Irritable Bowel Syndrome—Wikipedia, dated Sep. 16, 2020. 33 pages, https://en.wikipedia.org/wiki/Irritable_bowel_syndrome.
Israeli Office Action for Application No. 244391 filed on Mar. 2, 2016 on behalf of SOFAR S.P.A. dated Jun. 24, 2020 4 pages (English + Original).
Israeli Office Action for Application No. 269107 filed on Sep. 3, 2019 on behalf of SOFAR S.P.A. dated May 17, 2020 5 pages (English + Original).
Italia iI Ministero della Salute (*Linee Guida su Probiotici e Prebiotici rev.*May 2013).
Jacobsen et al., "Screening of Probiotic Activities of Forty-Seven Strains of *Lactobacillus* spp. By In Vitro techniques and Evaluation of the Colonization Ability of Five Selected Strains in Humans" Applied and Environmental Microbiology, Nov. 1999, p. 4949-4956. 8 pages.
Japanese Office Action for JP Application No. 2016564193 filed on Apr. 22, 2015 on behalf of SOFAR S.P.A. dated Feb. 18, 2020 11 pages (English + Original).
Langhorst J. et al., "Distinct patterns of short-chain fatty acids during flare in patients with ulcerative colitis under treatment with mesalamine or a herbal combination of myrrh, chamomile flowers, and coffee charcoal: secondary analysis of a randomized controlled trial" European Journal of Gastroenterology & Hepatology, Feb. 2020, 6 pages.
Larsen et al., "Predominant genera of fecal microbiota in children with atopic dermatitis are not altered by intake of probiolic bacteria Lactobacillus acidophilus NCFM and *Bifidobacterium animalis* subsp. lacis Bi-07,"FEMS Microbiol Ecol 75: 482-496 (2011).
Laws et al., "Biosynthesis, characterization, and design of bacterial exopolysacharides from lactic acid bacteria", *Biotechnology Advances*. vol. 19,2001. pp. 597-625.
Intermountain Healthcare. 2015. Irritable Bowel Syndrome (IBS). Retrieved from: https://intermountainhealthcare.org/services/gastroenterology/conditions/irritable-bowel-svndrome/. 2015. 3 pages.
Magnusson M. et al., "The Anti-inflammatory Immune Regulation Induced by Butyrate is Impaired in Inflamed Intestinal Mucosa from Patients with Ulcerative Colitis" Inflammation, Apr. 2020, 11 pages.
Martin R. et al. "Role of commensal and probiotic bacteria in human health: a focus on inflammatory bowel disease", Microbial Cell Factories 2013, 12: 71.
Matthes H. et al. "Clinical trial: probiotic treatment of acute distal ulcerative colitis with rectally administered *Escherichia Coli* Nissle 1 917 (EcN)", BMC Complementaty and Alternative Medicine 2010, 10: 13.
Mazzuoli S. et al. "Definition and evaluation of mucosal healing in clinical practice", Digestive and Liver Disease 2013, 45, 969-977.
Mcfarland, et al., "Strain-Specificity and Disease-Specificity of Probiotic Efficacy: A Systematic Review and Meta-Analysis," Frontiers in Medicine, May 7 2018. 14 Pages.
Mexican Office Action for MX Application No. MX/a/2016/002766 filed on Sep. 5, 2014 on behalf of SOFAR S.P.A. dated Aug. 13, 2020 10 pages (English + Original).
Michail et al., "Gut Microbiota is Not Modified by Randmized, Double-Blind, Placebo-Controlled Trial of VSL #3 in Diarrhea-Predominant Irritable Bowel Syndrome". (Probiotics & Antimicro Prot. (2011) 3: 1-7).

Montalto M. et al., "Clinical trial: the effects of a probiotic mixture on non-steroidal anti-inflammatory drug enteropathy—a randomized, double-blind, cross-over, placebo-controlled study" *Aliment Pharmacol Ther*,2010, pp. 209-214, 6 pages.
Muyzer et al., "Profiling of Complex Microbial Populations by Denaturing Gradient Gel Electrophoresis Analysis of Polymerase Chain Reaction-Amplified Genes Coding for 16S rRNA," Applied and Environmental Microbiology 59: 595-700(1993).
Necas J. et al. "Hyaluronic acid (hyaluronan): a review", Veterinarni Medicina, 2008, 53(8): 397-411.
Neiwert et al., "Structural Investigation of rhamnose-rich polysaccharides from *Streptococcus dysgalactiae* bovine mastitis isolate" Carbohydrate Research, vol. 389, 2014. pp. 192-195.
Non-Final Office Action for U.S. Appl. No. 16/308,330, filed Dec. 7, 2018 on behalf of SOFAR S.P.A., dated May 14, 2020. 23 Pages.
Non-Final Office Action for U.S. Appl. No. 15/305,470, filed Oct. 20, 2016 on behalf of SOFAR SPA, dated Aug. 22, 2019. 8 pages.
Non-Final Office Action for U.S. Appl. No. 16/301,361, filed Nov. 13, 2018 on behalf of SOFAR S.P.A. dated May 8, 2020 20 pages.
Non-Final Office Action for U.S. Appl. No. 14/916,959, filed Mar. 4, 2016 on behalf of SOFAR S.P.A. dated Mar. 13, 2020 25 pages.
Non-Final Office Action for U.S. Appl. No. 14/916,959, filed Mar. 4, 2016 on behalf of SOFAR SPA, dated Aug. 31, 2017. 27 pages.
Non-Final Office Action for U.S. Appl. No. 14/916,959, filed Mar. 4, 2016 on behalf of SOFAR SPA, dated Nov. 19, 2018. 15 pages.
Non-Final Office Action for U.S. Appl. No. 15/305,470, filed Oct. 20, 2016 on behalf of SOFAR SPA, dated Mar. 26, 2018. 10 pages.
Office Action in Corresponding Japanese Patent Application No. 2016-564193, dated Apr. 2, 2019.
Oliva S. et al. "Randomised clinical trial: the effectiveness of Lactobacillus Reuteri ATCC 55730 rectal enema in children with active distal ulcerative colitis", Aliment. Pharmacol. Ther. 2012, 35: 327-334.
Orlando A. et al. "Clinical implications of mucosal healing in the management of patients with inflammatory bowel disease", Digestive and Liver Disease 2013, 45, 986-991.
Pituch A. et al., "Butyric acid in functional constipation" *Przeglad Gastroenterologiczny*,2013, 4 pages.
Polak-Berecka et al., "Physiocochemical characterization of exopolysaccharides produced by lactobacillus rhamnosus on various carbon sources", *Carbohydrate Polymers*, vol. 117, 2015. pp. 501-509.
Pozuelo M. et al., "Reduction of butyrate and methane producing microorganisms in patients with Irritable Bowel Syndrome" *Nature Scientific Reports*,Apr. 2015, 12 pages.
Price R.D. et al. "Hyaluronic acid: the scientific and clinical evidence", Journal of Plastic, Reconstructive & Aesthetic Surgery2007, 60: 1110-1119.
Ralf Jager et al., "Probiotic Administration Increases Amino Acid Absorption from Plant Protein: a Placebo-Controlled, Randomized, Double-Blind, Multicenter, Crossover Study," Probiotics and Antimicrobial Proteins, 2020. 10 Pages.
Ringel-Kulka T. et al., "Short Chain Fatty Acids and Intestinal Transit in Patients With Irritable Bowel Syndrome and Healthy Controls" *AGA Abstracts*,May 2012, 1 page.
Sanlibaba et al., "Exopolysaccharides production by lactic acid bacteria", *Applied Microbiology, vol. 2*,May 20, 2016.
Sasaki M.. et al., "Transglucosidase improves the gut microbiota profile of type 2 diabetes mellitus patients: a randomized double-blind, placebo-controlled study" *BMC Gastroenterology*, 13:81,2013.
Scaldaferri F. et al. "Gut microbial flora, prebiotics and probiotics in IBD: their current usage and utility", BioMed Research International 2013, 9 pages.
Scarpellini E. et al., "Efficacy of butyrate in the treatment of diarrhea-predominant irritable bowel syndrome" Digestive and Liver Disease, 2007, 4 pages.
Shi Y. et al., "Function and clinical implications of short-chain fatty acids in patients with mixed refractory constipation" Association of Coloproctology of Great Britain and Ireland, Feb. 2016, 8 pages.
Siew Chien NG et al., "Effect of probiotic bacteria on the intenstinal microbiota in irritable bowel syndrome" Journal of gastroenterology and hepatology. 2013.

(56) References Cited

OTHER PUBLICATIONS

Smokvina T. et al "Lactobacillus paracasei Comparative Genomics: Towards Species Pan-Genome Definition and Exploitation of Diversity," PLOS ONE, July 19, 2013. 16 Pages.

Spiller et al., "Randomized double blind placebo-controlled trial of *Saccharomyces cerevisiae* CNCM I-3856 in irritable bowel syndrome: improvement in abdominal pain and bloating in those with predominant constipation" *Unlted European Gastroenterology Journal*. 2016.

Stuknyte M. et al., "Potential immunomodulatory activity of bovine casein hydrolysates produced after digestion with proteinases of lactic acid bacteria" *International Dairy Journal*, 21(2011) pp. 763-769.

Sun Q. et al., "Alterations in fecal short-chain fatty acids in patients with irritable bowel syndrome" *Systematic Review and Meta-Analysis*, Jan. 2019, 12 pages.

Third Chinese Office Action for CN Application No. 2014800492964 filed on Sep. 5, 2014 on behalf of SOFAR S.P.A. dated Mar. 18, 2020 13 pages (English + Original).

Turco F. et al., Bacterial stimuli activate nitric oxide colonic mucosal production in diverticular disease. Protective effects of L. casei DG (*Lactobacillus paracasei* CNCM I-1572) UEG Journal, Nov. 2016, 10 pages.

Turco F. et al., "Enteroglial-derived S1008 protein integrates bacteria-induced Toll-like receptor signalling in human enteric glial cells" GUT Neurogastroenterology, vol. 63, Mar. 2014, Originallv Published online Jan. 3, 2013, 12 pages.

Turnbaugh et al., "The Effect of Diel on the Human Gut Microbiome: A Metagenomic Analysis in Humanized gnolobiotic Mice," Sci Transl Med: (2009).

Tursi A. et al., "Assessment of Fecal Microbiota and Fecal Metabolome in Symptomatic Uncomplicated Diverticular Disease of the Colon" *J. Clin Gastroenterol*, Oct. 2016, 4 pages.

Tursi A. et al., "Fecal Microbiota, Fecal and Urinary Metabolic Profiling and Symptomatic Uncomplicated Diverticular Disease of the Colon" *Digestive and Liver Disease*, 2017, 1 page.

Tursi A. et al., "Natural History of Symptomatic Uncomplicated Diverticular Disease: A 13-Year Prospective Study" *AGA Abstracts*, Apr. 2017, 1 page.

Tursi et al., "Balsalazide and/or high-potency probiotic mixture (VSL#3) in maintaining remission after attack of acute, uncomplicated diverticulitis of the colon", International Journal of Colorectal Disease; Clinical and Molecular Gastroenterology an Surgery, Sprinfer, Berlin, DE. vol. 22, No. 9, Mar. 28, 2007. pp. 1103-1108.

Tursi et al., "Mesalazine and/or Lactobacillus Casei in maintaining Long-term Remission of Symptomatic Uncomplicated Diverticular Disease of the Colon" Original Paper. Hepato-Gastroenterology. 2008, 55; 916-920.

Tursi et al., "Mesalazine and/or Lactobacillus casei in preventing recurrence of symptomatic uncomplicated diverticular disease of the colon: A Prospective, randomized, open-label study", Journal of Clinical Gastroenterol, Raven Press LTD, NY, New York. vol. 40, No. 2, Apr. 1, 2006. pp. 312-316.

U.S. National Library of Medicine, "Effect of Lactobacillus Casei DG (Enterolactis Plus) in Patient with irritable Bowel Syndrome: a Pilot Study", ClinicalTriaals.gov, Feb. 11, 2015.

U.S. National Library of Medicine Efficacy Evaluation of a Commercial Preparation Containing Lactobacillus Casei DC on the Reduction of the Painful Symptoms Related to the Irritable Bowel Syndrome (IBS). *A Pilot Clinical Study*.Feb. 28, 2014.

Vinogradov et al., "Structural studies of the rhamnoseirch cell wall polysaccharide of lactobacillus casei BL23" *Carbohydrate Research* vol. 435, Oct. 8, 2016. pp. 156-161.

"Why VSL#3" (Obtained from https://vsl3.com/hcp/vsl-info on Aug. 22, 2017, 4 pages.

Worthley et al. "A human, double-blind, placebo-controlled, crossover trial of prebiotic, probiotic, and symbiotic supplementation: effects on luminal, inflammatory, epigenetic, and epithelial biomarkers of colorectal cancer" (Am J Clin Nutr 2009; 90; 578-86).

Written Opinion for International Application No. PCT/IB2014/064284 filed on Sep. 5, 2014 on behalf of SOFAR SPA, dated Jan. 26, 2015. 7 pages.

Written Opinion for International Application No. PCT/IB2017/052850 filed on May 15, 2017 on behalf of SOFAR SPA, dated Aug. 17, 2017. 6 pages.

Written Opinion for International Application No. PCT/IB2017/053389 filed on Jun. 8, 2017 on behalf of SOFAR SPA, dated Oct. 6, 2017. 7 pages.

Written Opinion for International Application No. PCT/IB2017/057576 filed on Dec. 1, 2017 on behalf of SOFAR SPA, dated Feb. 22, 2018. 8 pages.

Written Opinion for International Application No. PCT/IB2017/057980 filed on Dec. 15, 2017 on behalf of SOFAR SPA, dated Mar. 19, 2018. 8 pages.

Written Opinion for International Application PCT/IB2015/052938 filed on Apr. 22, 2015 on behalf of SOFAR SPA, dated Jul. 31, 2015. 5 pages.

Zhang et al., "Isolated exopolysaccharides from lactobacillus rhamnosus GG alleviated adipogenesis mediated by TLR2 in mice" *Scientific reports*. vol. 6, Oct. 27, 2016.

Zheng, L. et al. "Regulation of colonic epithelial repair in mice by toll-like receptors and hyaluronic acid," Gastroenterology 2009: 137 2041-2051.

Zhuang M. et al., "Abundance of probiotics and butyrate-production microbiome manages constipation via short-chain fatty acids production and hormones secretion" Molecular Nutrition & Food Research, Jul. 2019, 41 pages.

Zhuang M. et al., "Systematic Review and Meta-analysis: Short-Chain Fatty Acid Characterization in Patients With Inflammatory Bowel Disease" *Inflammatory Bowel Disease*, Nov. 2019, 13 pages.

Australian Examination Report for AU Application No. 2017263294 filed on May 15, 2017 on behalf of SOFAR S.P.A. dated Oct. 30, 2020 5 pages.

Balzaretti S. et al., "A novel hetero-exopolysaccharide mediates the recognition of Lactobacillus paracasei DG by the immune system" Pharmabiotics Conference2015, Paris, Oct. 29-30, 2015, 1 page.

Bienenstock J et al., "New insights into probiotic mechanisms" *Gut Microbes*, vol. 4 Issue 2, Apr. 2013, 7 pages.

Brussow H. "Problems with the concept of gut microbiota dysbiosis" Microbial Biotechnology. vol 13(2). 2020. pp. 423-434.

Canadian Examination Search Report for CA Application No. 2,923,390 filed on Sep. 5, 2014 on behalf of SOFAR S.P.A. dated Jan. 26, 2021 4 pages.

Canadian Office Action for CA Application No. 2,923,392 filed on Sep. 5, 2014 on behalf of SOFAR S.P.A. dated Apr. 1, 2021 4 pages.

Canani R. B. et al., "Potential beneficial effects of butyrate in intestinal and extraintestinal diseases" World Journal of Gastroenterology, vol. 17 No. 12, Mar. 2011, 10 pages.

Chinese Decision of Rejection for CN Application No. 2014800492964 filed on Sep. 5, 2014 on behalf of SOFAR S.P.A. dated Dec. 9, 2020 (English + Original) 12 pages.

Chooi E. et al., "Chronic atrophic gastritis is a progressive disease: analysis of medical reports from Shanghai (1985-2009)" Singapore Med J, 2012, 53 (5), pp. 318-324.

Colledge H. "Atrophic Gastritis: Causes. Symptoms, & Treatment" *Healthline*, Sep. 2018, 5 pages.

Colombian Office Action for CO Application No. NC2018/0010950 filed on May 15, 2017 on behalf of SOFAR S.P.A. dated May 3, 2021 9 pages (English + Original).

Colombian Office Action for CO Application No. NC2018/0010954 filed on Nov. 1, 2018 on behalf of SOFAR S.P.A. dated Feb. 5, 2021 9 pages (Partial English + Original).

Colombian Office Action for CO Application No. NC2019/0007116 filed on Jul. 2, 2019 on behalf of SOFAR S.P.A. dated Jan. 15, 2021 19 pages (English + Original).

Communication pursuant to Article 94(3) EPC for EP Application No. 14790322.3 filed on Sep. 5, 2014 on behalf of SOFAR S.P.A. dated Jan. 11, 2021 3 pages.

Cui Y. et al., "Revolution of Chronic Diarrhoea" China Medicine, Science, and Technology Publishing House, 1st edition, Jan. 2013, pp. 19-23 (Original + Partial Google Translation) 14 pages.

(56) References Cited

OTHER PUBLICATIONS

De Backer A. I. et al., "Intestinal stenosis from mesenteric injury after blunt abdominal trauma" Eur. Radiol., 1999, pp. 1429-1431.
Declaration for the self-archiving of the doctoral thesis for "Exploring Lactobacillius Paracasei Probiosis and Metabolic Potential" by Balzaretti, Silvia Dated: Nov. 20, 2015 4 pages (English + Original).
Gould M. et al., "Diabetic diarrhea" Current Gastroenterology Report, 2009, pp. 354-359 (Abstract only).
Israeli Office Action for IL Application No. 244391 filed on behalf of SOFAR S.P.A. dated Oct. 27, 2020 (English + Original) 4 pages.
Jarbrink-Sehgal M. E. et al., "Symptomatic Diverticulosis is Characterized by Loose Stools" *Clinical Gastroenterology and Hepatology*, 14: 1763-1770, Dec. 2016, 9 pages.
Koebnick C. et al., "Probiotic beverage containing Lactobacillus casei Shirota improves gastrointestinal symptoms in patients with chronic constipation" Can J Gastroenterol, vol. 17 No. 11, Nov. 2003, pp. 655-658.
Laval G. et al., "The use of steroids in the management of inoperable intestinal obstruction in terminal cancer patients: do they remove the obstruction?" Palliative Medicine, 2000, pp. 3-10.
Laws A. et al., "Determination of the structure and molecular weights of the exopolysaccharide produced by Lactobacillus acidophilus 5e2 when grown on different carbon feeds." *Carbohydr Res*.Feb. 4, 2008;343(2):301-7.
Mangili G. et al., "Palliative care for intestinal obstruction in recurrent ovarian cancer: a multivariate analysis" *BMJ Journals*,2005, 5 pages (Abstract Only).
Mexican Office Action for MX Application No. MX/a/2016/002766 filed on Sep. 5, 2014 onbehalf of SOFAR S.P.A. dated Mar. 18, 2021 10 pages (English + Original).
Miceli E. et al., "Common Features of Patients with Autoimmune Atrophic Gastritis" *Clinical Gastroenterology and Hepatology*,2012, pp. 812-814.
Non-Final Office Action for U.S. Appl. No. 14/916,959, filed Mar. 4, 2016 on behalf of SOFAR S.P.A. dated Apr. 13, 2021 33 pages.
Non-Final OfficeAction for U.S. Appl. No. 16/308,330, filed Dec. 7, 2018 on behalf ofSOFAR S.P.A. dated April 30, 2021. 38 Pages.
Notice of Allowance for U.S. Appl. No. 15/305,470, filed Oct. 20, 2016 on behalf of SOFAR S.P.A. dated Jun. 1, 2021 15 gages.
Notice of Allowance for U.S. Appl. No. 16/301,361, filed Nov. 13, 2018 on behalf of SOFAR S.P.A. dated Feb. 1, 2021 8 pages.
Notice of Allowance for U.S. Appl. No. 16/301,361, filed Nov. 13, 2018 on behalf of SOFAR S.P.A. dated May 3, 2021 9 pages.
Paoluzi O.A., et al. "Low efficacy of levofloxacin-doxycycline-based third-line tripletherapy for Helicobacter pylori eradication in Italy." *World Journal of Gastroenteroloqy*21 : 6698-705,Jun. 2015.
Restriction Requirement for U.S. Appl. No. 16/465,237, filed May 30, 2019 on behalf of SOFAR S.P.A. dated Dec. 21, 2020 8 pages.
Restriction Requirement for U.S. Appl. No. 16/467,797, filed Jun. 7, 2019 on behalf of SOFAR S.P.A. dated Jun. 15, 2021 6 pages.
Rodriguez-Castro K. I. et al., "Clinical manifestations of chronic atrophic gastritis" Acta Biomed. vol. 89, 2018, pp. 88-92.
Rosania R. et al. "Effect of probiotic or prebiotic supplementation on antibiotic therapy in the small intestinal bacterial overgrowth: a comparative evaluation." Curr Clin Pharmacol . May 2013;8(2):169-72. 5 pages.
Scarpignato C. et al., "Management of colonic diverticular disease in the third millennium: Highlights from a symposium held during the United European Gastroenterology Week 2017" Therapeutic Advances in Gastroenterology, vol. 11, Mar. 2018, pp. 1-21.
Screenshot from the web-archive of the Milano University, Nov. 23, 2015, 2 pages (English + Original).
Tuohy K.M. et al., "Survivability of a probiotic Lactobacillus casei in the gastrointestinal tract of healthy human volunteers and its impact on the faecal microflora" *Journal of Applied Mircrobiology*,2007, pp. 1026-1032.
Wang Y. et al., "Emerging Infectious Diseases" Science and Technology Documents Publishing House, 1st edition, Jan. 2006, pp. 310-312 (Original + Partial Google Translation) 12 pages.
Watanabe I. et al., "KT-11" *Food Style 21*, vol. 17, No. 6, pp. 62-64,2013. 10 pages (Machine Translation + Original).
Wells D. "Gastritis Diet: What to Eat and What to Avoid" Healthline, Jul. 2020, 11 pages.
Brunkwall L. et al., "Self-reported bowel symptoms are associated with differences in overall gut microbiota composition and enrichment of Blautia in a population-based cohort" *Journal of Gastroenterology and Hepatology*, vol. 36, (2021), pp. 174-180.
Cicenia, A. et al., "Postbiotic Activities of Lactobacilli-derived Factors", J Clin Gastroenterol, vol. 48, Supp. 1, Nov./Dec. 2014, S18-S22 (5 pages).
Corrected Notice of Allowability for U.S. Appl. No. 16/465,237, filed May 30, 2019, on behalf of SOFAR S.P.A. dated Jun. 22, 2022. 20 Pages.
International Preliminary Report on Patentability for International Application No. PCT/IB2020/060412 filed on Nov. 5, 2020 on behalf of SOFAR S.P.A. dated May 10, 2022 7 pages.
International Search Report and Written Opinion for International Application No. PCT/IB2020/060412 filed on Nov. 5, 2020 on behalf of SOFAR S.P.A. dated Mar. 4, 2021 10 pages.
Metagenomics—Wikipedia, the free encyclopedia, Dated: May 16, 2013 https://web.archive.org/web/20130516095714/https://en.wikipedia.org/wiki/Metagenomics , 16 pages.
Notice of Allowance for U.S. Appl. No. 15/305,470, filed Oct. 20, 2016, on behalf of SOFAR SPA, dated Jun. 9, 2022. 11 Pages.
Notice of Allowance for U.S. Appl. No. 16/465,237, filed May 30, 2019, on behalf of SOFAR S.P.A. dated Jun. 1, 2022. 15 Pages.
Notice of Allowance for U.S. Appl. No. 16/467,797, filed Jun. 7, 2019 on behalf of SOFAR S.P.A. dated Jul. 15, 2022 13 pages.
Qin J. et al., "A human gut microbial gene catalogue established by metagenomic sequencing" *Nature*, vol. 46, Mar. 2010, pp. 59-67.
Tsilingiri, K. et al., "Probiotic and postbiotic activity in health and disease: activity comparison on a novel polarised ex-vivo organ culture method", Gut 2012; 61:1007-1015 (9 pages).
Zhernakova A. et al., "Population-based metagenomics analysis reveals markers for gut microbiome composition and diversity" Science, vol. 352, Apr. 2016, 15 pages.
Allowance of the Brazilian patent application BR 11 2016 005059 2 published in the Official Bulletin $n^{ul;1oul;0}$2651 of Oct. 26, 2021 (Portuguese Only).
Azad M.D.A.K. et al., "Immunomodulatory Effects of Probiotics on Cytokine Profiles" Biomed Research International, vol. 2018, Oct. 2018, pp. 1-10.
Bacteriotherapy—Merriam-Webster Medical Dictionary, Archive Date: Apr. 26, 2016, 6 pages.
Bedford A. et al., "Implications of butyrate and its derivatives for gut health and animal production" *Animal Nutrition*, vol. 4, 2018, pp. 151-159.
Borycka-Kiciak K. et al., "Butyric acid—a well-known molecule revisited" *Gastroenterology Rev*, vol. 12 No. 2, 2017, pp. 83-89.
Canadian Office Action for CA Application No. 2,923,390 filed on Sep. 5, 2014 on behalf of SOFAR S.P.A. dated Nov. 29, 2021 5 pages.
Capsule (Pharmacy)—Wikipedia, the free encyclopedia, Archive Date: Apr. 10, 2016, 4 pages.
Cheng A. et al., "Polyphenols from blueberries modulate inflammation cytokines in LPS-induced RAW264.7 macrophages", *Acta. Paediatrica. Supplement*, Elsevier, vol. 69, Jun. 2014, pp. 382-387.
Chinese Office Action for CN Application No. 201780029401.1 filed on May 15, 2017 on behalf of SOFAR S.P.A. dated Dec. 15, 2021 (English + Original) 24 pages.
Colombian Office Action for CO Application No. NC2018/0010950 filed on May 15, 2017 on behalf of SOFAR S.P.A. dated Oct. 14, 2021 (Partial English + Original) 9 pages.
Colombian Office Action for CO Application No. NC2019/0007116 filed on Jul. 2, 2019 on behalf of SOFAR S.P.A. dated Sep. 29, 2021 12 pages (English + Original).
Connors J. et al., "The Role of Succinate in the Regulation of Intestinal Inflammation" *Nutrients*, vol. 11 No. 25, 2019, 12 pages.
Corrected Notice of Allowability for U.S. Appl. No. 15/305,470, filed Oct. 20, 2016, on behalf of SOFAR SPA, dated Feb. 25, 2022. 3 Pages.

(56) References Cited

OTHER PUBLICATIONS

Corrected Notice of Allowability for U.S. Appl. No. 15/305,470, filed Oct. 20, 2016 on behalf of SOFAR S.P.A. dated Jan. 10, 2022 4 pages.
Cui J. et al., "NMR-based metabonomics and correlation analysis reveal potential biomarkers associated with chronic atrophic gastritis" *Journal of Pharmaceutical and Biomedical Analysis*, vol. 132, 2017, pp. 77-86.
Dore J. et al., "The Human Intestinal Microbiota; From Phylogenetics to Functional Metagenomics" *Old Herborn University*, 2010, pp. 15-26.
Dysbiosis—Wikipedia, the free encyclopedia, Dated: March 31, 2014 https://web.archive.org/web/20140331225522/http://en.wikipedia.org/wiki/Dysbiosis , 4 pages.
Feng W. et al., "Sodium Butyrate Attenuates Diarrhea in Weaned Piglets and Promotes Tight Junction Protein Expression in Colon in a GPR109A-Dependent Manner" *Cellular Physiology and Biochemistry*, vol. 47, 2018, pp. 1617-1629.
Final Office Action for U.S. Appl. No. 16/308,330, filed Dec. 7, 2018, on behalf of SOFAR S.P.A. dated Feb. 9, 2022. 22 Pages.
Final Office Action for U.S. Appl. No. 14/916,959, filed Mar. 4, 2016 on behalf of SOFAR S.P.A. dated Dec. 29, 2021. 29 Pages.
Franco V. "Effectiveness of an association of a cranberry dry extract, D-mannose, and the two microorganisms Lactobacillus plantarum LP01 and Lactobacillus paracasei LPC09 in women affected by cystitis: a pilot study." *US National Library of Medicine*, Nov. 2014, 6 pages.
Gwiazdowska D. et al., "The impact of polyphenols on Bifidobacterium growth", Acta Biochimica Polonica, vol. 62 No. 4, Jan. 2015, 8 pages.
Haenel H. "Human Normal and Abnormal Gastrointestinal Flora" *American Journal of Clinical Nutrition*, vol. 23 no. 11, Nov. 1970, pp. 1433-1439.
Hajjar R. et al., "The role of butyrate in surgical and oncological outcomes in colorectal cancer" *American Journal of Physiology*. vol. 320. Jan. 2021, pp. G601-G608.
Hakansson A. et al., "Blueberry husks, rye bran and multi-strain probiotics affect the severity of colitis induced by dextran sulphate sodium" *Scandinavian Journal of Gastroenterology*, vol. 44 No. 10, Jan. 2009, pp. 1213-1225.
Hurst N.R. et al., "The Short Chain Fatty Acids, butyrate and Propionate, have Differential Effects on the Motility of the Guinea Pig Colon" *Neurogastroenterol Motil.*, vol. 26 No. 11, Nov. 2014, pp. 1586-1596.
Iebba V. et al., "Eubiosis and Dysbiosis: the two sides of the microbiota" *New Microbiologica*, vol. 39, 2016, pp. 1-12.
International Preliminary Report on Patentability for International Application No. PCT/IB2020/058774 filed on Sep. 21, 2020 on behalf of SOFAR S.P.A. dated Mar. 15, 2022 6 pages.
International Preliminary Report on Patentability for International Application No. PCT/IB2020/058769 filed on Sep. 21, 2020 on behalf of SOFAR S.P.A. dated Mar. 15, 2022 6 pages.
International Preliminary Report on Patentability for International Application No. PCT/IB2020/058777 filed on Sep. 21, 2020 on behalf of SOFAR S.P.A. dated Mar. 15, 2022 6 pages.
International Preliminary Report on Patentability for International Application No. PCT/IB2020/058778 filed on Sep. 21, 2020 on behalf of SOFAR S.P.A. dated Mar. 15, 2022 6 pages.
International Search Report and Written Opinion for International Application No. PCT/IB2020/058778 filed on Sep. 21, 2020 on behalf of SOFAR S.P.A. dated Feb. 18, 2021 8 pages.
International Search Report and Written Opinion for International Application No. PCT/IB2020/058769 filed on Sep. 21, 2020 on behalf of SOFAR S.P.A. dated Feb. 18, 2021 8 pages.
International Search Report and Written Opinion for International Application No. PCT/IB2020/058774 filed on Sep. 21, 2020 on behalf of SOFAR S.P.A. dated Dec. 8, 2020 8 pages.
International Search Report and Written Opinion for International Application No. PCT/IB2020/058777 filed on Sep. 21, 2020 on behalf of SOFAR S.P.A. dated Apr. 20, 2021 26 pages.
John Hopkins Medicine—Fecal Transplantation (Bacteriotherapy), John Hopkins Division of Gastroenterology and Hepatology, Archive Date: Apr. 2016, 2 pages.
Koradia P. et al., "Probiotic and cranberry supplementation for preventing recurrent uncomplicated urinary tract infections in premenopausal women: a controlled pilot study" *Expert Review of Anti-Infective Therapy*, vol. 17 No. 9, Sep. 2019, pp. 733-740.
Krokowicz L. et al., "Sodium butyrate and short chain fatty acids in prevention of travellers, diarrhoea—a randomized prospective study" *Travel Medicine and Infectious Disease*, Aug. 2013, 17 pages.
Lacombe A. et al., "The potential of berries to serve as selective inhibitors of pathogens and promoters of beneficial microorganisms" *Food Quality and Safety*, vol. 1 No. 1, Mar. 2017, pp. 3-12.
Le Noci V. et al., "Modulation of Pulmonary Microbiota by Antibiotic or Probiotic Aerosol Therapy: A Strategy to Promote Immunosurveillance against Lung Metastases" *Cell Reports*, vol. 24 No. 13. Sep. 2018, pp. 3528-3538.
Mexican Office Action for MX Application No. MX/a/2016/022766 filed on Sep. 5, 2014 on behalf of SOFAR S.P.A. dated Oct. 26, 2021 (Partial English + Original) 12 pages.
Mileo A.M. et al., "Polyphenols: Immunomodulatory and Therapeutic Implication in Colorectal Cancer" *Frontiers in Immunology*, vol. 10 Apr. 2019, 10 pages.
Milko R. et al., "Survival of L. casei DG (CNCMI1572) in the gastrointestinal tract of a healthy paediatric population", *European Journal of Nutrition, Steinkopff Verlag*, vol. 58 No. 8, Nov. 2018, 10 pages.
Nanau R.M. et al., "Nutritional and Probiotic Supplementation in Colitis Models" *Digestive Diseases and Sciences, Kluwer Academic Publishers-Plenum Publishers*, vol. 57 No. 11, Jun. 2012, pp. 2786-2810.
Non-Final Office Action for U.S. Appl. No. 16/467,797, filed Jun. 6, 2019 on behalf of SOFAR S.P.A. dated Dec. 14, 2021 35 pages.
Non-Final Office Action for U.S. Appl. No. 17/090,669, filed Nov. 5, 2020, on behalf of SOFAR S.P.A. dated Feb. 17, 2022. 45 Pages.
Notice of Allowance for U.S. Appl. No. 15/305,470, filed Oct. 20, 2016 on behalf of SOFAR S.P.A. dated Feb. 15, 2022 6 pages.
Notice of Allowance for U.S. Appl. No. 15/305,470, filed Oct, 20, 2016, on behalf of SOFAR SPA, dated Nov. 3, 2021. 8 Pages.
Notice of Allowance for U.S. Appl. No. 16/301,361, filed Nov. 13, 2018, on behalf of SOFAR S.P.A. dated Mar. 30, 2022. 11 Pages.
Patel, R., et a., "New Approaches for Bacteriotherapy: Prebiotics, New-Generation Probiotics, and Synbiotics," *Clinical Infectious Diseases*, vol. 60, Issue supplement 2, May 15, 2015. pp. S108-S121. 15 Pages. https://doi.org/10.1093/cid/civ177.
Rajendran V.M. et al., "Na-H Exchanger Isoform-2 (NHE2) Mediates Butyrate-dependent Na+ Absorption in Dextran Sulfate Sodium (DSS)-induced Colitis" *Journal of Biological Chemistry*, vol. 290 No. 42, Oct. 2015, 10 pages.
Saez-Lara M.J. et al., "The Role of Probiotic Lactic Acid Bacteria and Bifidobacteria in the Prevention and Treatment of Inflammatory Bowel Disease and Other Related Diseases: A systematic review of randomized human clinical trials" *Biomed Research International*, vol. 2015, Jan. 2015, pp. 1-15.
Salvetti E. et al., "The Genus Lactobacillus: A Taxonomic Update" *Probiotics & Antimicro. Prot.*, Nov. 2012, vol. 4, pp. 217-226.
Tsimmerman Y. S. "Eubiosis and Dysbiosis of Gastrointestinal Tract: Myths and Reality" *Perm State Medical Academy*, 2013, 27 pages.
Xu J. et al., "Intake of blueberry fermented by lactobacillus plantarum affects the guy microbiota of L-name treated rats" *Evidence-Based Complementary and Alternative Medicine*, vol. 2013, Jan. 2013, pp. 1-9.
Xue H. Lactose-Induced Chronic Diarrhea Results from Abnormal Luminal Microbial Fermentation and Disorder of Ion Transport in the Colon *Frontiers in Physiology*, vol. 11, Jul. 2020, pp. 1-14.
Yehua Y. "Mixed fermentation of blueberry pomace with L. rhamnosus GG and ingredient, antioxidant activity and health-promoting benefits", *Food and Chemical Toxicology*, vol. 131, 2019, 8 pages.
Yoshida Y. et al., "Oral administration of Lactobacillus plantarum Lq80 and Megasphaera elsdenii iNP-001 induces efficient recovery

(56) References Cited

OTHER PUBLICATIONS from mucosal atrophy in the small and the large intestines of weaning piglets" *Animal Science Journal*, vol. 80, 2009, pp. 709-715.
Yuanning S. et al., "Analysis of Lactic Acid Bacteria Protein Dissolution and Aroma Production Ability" Chinese Brew, vol. 33 No. 3, Dec. 31, 2014 (English Abstract + Original) 4 pages.
Australian Examination Report for AU Application No. 2017367302 filed on Dec. 1, 2017 on behalf of SOFAR S.P.A. dated Jul. 23, 2021 4 pages.
Bassi R. "Mesalazine + Lactobacillus paracasei CNCMI1572 vs Mesalazine alone in preventing recurrence of symptom of diverticular disease: a prospective, randomize, open-label study." *Colorectal Disease*, 2019 1 pages.
Bassi R. "Preventing recurrence of symptomatic diverticular disease of the colon: mesalazine with or without Lactobacillus case DG: a prospective randomized, open label study." European Society of Coloproctology, 2015, 1 page.
Chilean Office Action for CL Application No. 201901493 filed on Dec. 1, 2017 on behalf of SOFAR S.P.A. dated May 6, 2021 24 gages (English + Original).
Chinese Office Action for CN Application No. 201480049288X filed on Sep. 5, 2014 on behalf of SOFAR S.P.A. dated Aug. 12, 2021 (English + Original) 15 pages.
Colombian Office Action for CO Application No. NC2018/0010954 filed on Jun. 2, 2019 on behalf of SOFAR S.P.A. dated Jun. 30, 2021 8 pages (Partial English + Original).
Communication pursuant to Article 94(3) EPC for EP Application No. 17817173.2 filed on Dec. 1, 2017 on behalf of SOFAR S.P.A. dated Sep. 29, 2021 6 pages.
Eurasian Office Action for EA Application No. 202090097/28 filed on Sep. 5, 2014 on behalf of SOFAR S.P.A. dated Aug. 16, 2021 (English + Original) 10 pages.
Notice of Allowance for U.S. Appl. No. 15/305,470, filed Oct. 20, 2016, on behalf of SOFAR SPA, dated Sep. 8, 2021. 8 Pages.
Restriction Requirement for U.S. Appl. No. 17/090,669, filed Nov. 5, 2020, on behalf of SOFAR S.P.A. dated Sep. 3, 2021. 7 Pages.
World Gastroenterology Organisation Global Guidelines "Probiotics and prebiotics" Feb. 2017, 35 pages.
Colombian Office Action for Colombian Application No. NC2019/0006257 filed on Dec. 15, 2017 on behalf of SOFAR S.P.A. dated May 13, 2021 3 pages (English + Original).
Non-Final Office Action for U.S. Appl. No. 16/465,237, filed May 30, 2019, on behalf of SOFAR S.P.A. dated Jul. 9, 2021. 37 Pages.
Notice of Allowance for U.S. Appl. No. 16/301,361, filed Nov. 13, 2018, on behalf of SOFAR S.P.A. dated Aug. 4, 2021. 11 Pages.
Zhang, Z., et al., "Isolated exopolysaccharides from Lactobacillus rhamnosus GG alleviated adipogenesis mediated by TLR2 in mice," *Sci Rep*6, 36083, Oct. 27, 2016. 13 Pages. https://doi.org/10.1038/srep36083.
Cure—Wikipedia, the free encyclopedia. Date: May 12, 2013 4 pages https://web.archive.org/web/20130512085159/httgs://en.wikigediaorg/wiki/Remission_(medicine).
De Almada C. N. et al., "Paraprobiotics: Evidences on their ability to modify biological responses, inactivation methods and perspectives on their application in foods" *Trends in Food Science & Technology*, vol. 58, 2016, pp. 96-114.
Final Office Action for U.S. Appl. No. 17/090,669, filed Nov. 5, 2020 on behalf of SOFAR S.P.A., dated Nov. 9, 2022. (15 pages).
Lee Y. K. et al., "Handbook of Probiotics and Prebiotics" Wiley, 2009, Excerpt: 3 pages.
Non-Final OA Office Action for U.S. Appl. No. 16/308,330, filed Dec. 7, 2018, on behalf of SOFAR S.P.A. dated Sep. 1, 2022. 26 Pages.
Non-Final Office Action for U.S. Appl. No. 14/916,959, filed Mar. 4, 2016, on behalf of SOFAR S.P.A. dated Sep. 30, 2022. 34 Pages.
Non-Final Office Action for U.S. Appl. No. 16/467,797, filed Jun. 7, 2019, on behalf of SOFAR S.P.A. dated Sep. 14, 2022. 5 Pages.
Notice of Allowance for U.S. Appl. No. 16/465,237, filed May 30, 2019 on behalf of SOFAR S.P.A. dated Nov. 2, 2022 13 pages.

Patel R. M. et al., "Therapeutic Use of Prebiotics, Probiotics, and Postbiotics to Prevent Necrotizing Enterocolitis: What is the Current Evidence?" *Clin Perinatal*, vol. 40, Mar. 2013, pp. 1-20.
Poortmans J. R. et al., "Protein metabolism and physical training: any need for amino acid supplementation?" *Nutrire*, vol. 41 No. 21, 2016, pp. 1-17.
Santigosa E. et al., "Modifications of intestinal nutrient absorption in response to dietary fish meal replacement by plant protein sources in sea bream (*Sparus aurata*) and rainbow trout (*Onchorynchus mykiss*)" Fish Nutrition Research Laboratory, 2011, 38 pages.
Tomar S. K. et al., "Role of probiotics, prebiotics, synbiotics, and postbiotics in inhibition of pathogens" *The Battle Against Microbial Pathogens: Basic Science, Technological Advances and Educational Programs*, 2015, pp. 717-732.
Tsilingiri K. et al., "Postbiotics: what else?" *Beneficial Microbes*, vol. 4 No. 1, Mar. 2013, pp. 101-107 (Abstract Only).
WHO Technical Report Series 935—Protein And Amino Acid Requirements in Human Nutrition, 2007, 284 pages.
Annex to Summons for EP Application No. 17 742 849.7 filed on Jun. 8, 2017 on behalf of SOFAR S.P.A., dated Feb. 23, 2023, 8 pages.
Annibale, B. et al., "Efficacy of *Lactobacillus paracasei* sub. paracasei F19 on abdominal symptoms in patients with symptomatic uncomplicated diverticular disease: A pilot study", Minerva Gastroentrologica E Dietologica, vol. 57, No. 1, Mar. 2011, 12 pages.
Arumugam, M., et al., "Enterotypes of the human gut microbiome," *Nature* 473: 174-180. May 12, 2011. 16 Pages. https://doi.org/10.1038/natur909944.
Brazilian Office Action for BR112018074795 filed on Jun. 8, 2017 on behalf of SOFAR S.P.A. dated Sep. 22, 2022 6 pages (Partial English Translation + Original).
Canadian Office Action for CA Application No. 2,923,390 filed on Mar. 4, 2016 on behalf of SOFAR S.P.A. dated Nov. 3, 2022, 4 pages.
Colombian Office Action for NC2018/0010954 filed on Nov. 1, 2018 on behalf of SOFAR S.P.A. dated Jan. 6, 2022 (English Translation + Original) 8 pages.
Corrected Notice of Allowability for U.S. Appl. No. 16/308,330, filed Dec. 7, 2018 on behalf of SOFAR S.P.A., dated Feb. 3, 2023. (6 pages).
Corrected Notice of Allowability for U.S. Appl. No. 17/090,669, filed Nov. 5, 2020 on behalf of SOFAR S.P.A., dated May 1, 2023. (2 pages).
Corrected Notice of Allowability for U.S. Appl. No. 17/090,669, filed Nov. 5, 2020 on behalf of SOFAR S.P.A., dated May 17, 2023. (3 pages).
Distrutti, Eleanora et al., "Gut microbiota role in irritable bowel syndrome: New therapeutic strategies", World J Gastroenterol, Feb. 21, 2016, 22(7), 2219-2241 (24 pages).
Final Office Action for U.S. Appl. No. 14/916,959, filed Mar. 4, 2016 on behalf of SOFAR S.P.A., dated Mar. 27, 2023 (31 pages).
Final Office Action for U.S. Appl. No. 16/467,797, filed Jun. 7, 2019 on behalf of SOFAR S.P.A., dated Mar. 3, 2023. (9 pages).
Hamady, M., et al., "Microbial community profiling for human microbiome projects: Tools, techniques, and challenges," *Genome Res.* 19: 1141-1152. Apr. 21, 2009. 12 Pages. doi:10.1101/gr.085464.108.
Kim, H.J. et al., "A randomized controlled trial of a probiotic combination VSL# 3 and placebo in irritable bowel syndrome with bloating", Neurogastroenterol Motil, Oct. 2005, 17(5), 687-696, (10 pages).
Lamiki, Pepu et al., "Probiotics in Diverticular Disease of the Colon: an Open Label Study", J. Gastrointestin Liaver Dis, Mar. 2010, Vo. 19, No. 1, pp. 31-36. (6 pages).
Notice of Allowance for U.S. Appl. No. 16/308,330, filed Dec. 7, 2018 on behalf of SOFAR S.P.A., dated Jan. 25, 2023. (11 pages).
Notice of Allowance for U.S. Appl. No. 16/308,330, filed Dec. 7, 2018 on behalf of SOFAR S.P.A., dated May 11, 2023. (9 pages).
Notice of Allowance for U.S. Appl. No. 17/090,669, filed Nov. 5, 2020 on behalf of SOFAR S.P.A., dated Apr. 24, 2023. (7 pages).

(56) References Cited

OTHER PUBLICATIONS

Riesenfeld, C.S., "Metagenomics: Genomic Analysis of Microbial Communities," *Annu. Rev. Genet.* 38: 525-52. Jul. 14, 2004. 30 Pages. doi: 10.1146/annurev.genet.38.072902.091216.

Summons to attend oral proceedings pursuant to Rule 115(1) EPC for EP Application No. 17 742 849.7 filed on Jun. 8, 2017 on behalf of SOFAR S.P.A., dated Feb. 23, 2023. 2 pages.

U.S. National Library of Medicine, Search of: "accepts healthy volunteers"—List Results, ClinicalTrials.gov, downloaded Feb. 19, 2023, https://clinicaltrials.gov/ct2/results?cond=&term=healthy&cntry=&sta. 4 pages.

Xu, J., "Microbial ecology in the age of genomics and metagenomics: concepts, tools, and recent advances" Molecular Ecology, Jun. 2006, 15(7), 1713-1731 (19 pages).

Yu, K., et al., "Metagenomic and Metatranscriptomic Analysis of Microbial Community Structure and Gene Expression of Activated Sludge," *PLoS ONE* 7(5): e38183. May 2012. 13 Pages. https://doi.org/10.1371/journal.pone.0038183.

Tursi et al., "Randomised clinical trial: mesalazine and/or probiotics in maintaining remission of symptomatic uncomplicated diverticular disease—a double-blind, randomised, placebo-controlled study," Aliment Pharmacol Ther 38: 741-751 (2013).

Office Action in corresponding Chinese Patent Application No. 201480049296.4, dated Aug. 27, 2019.

* cited by examiner

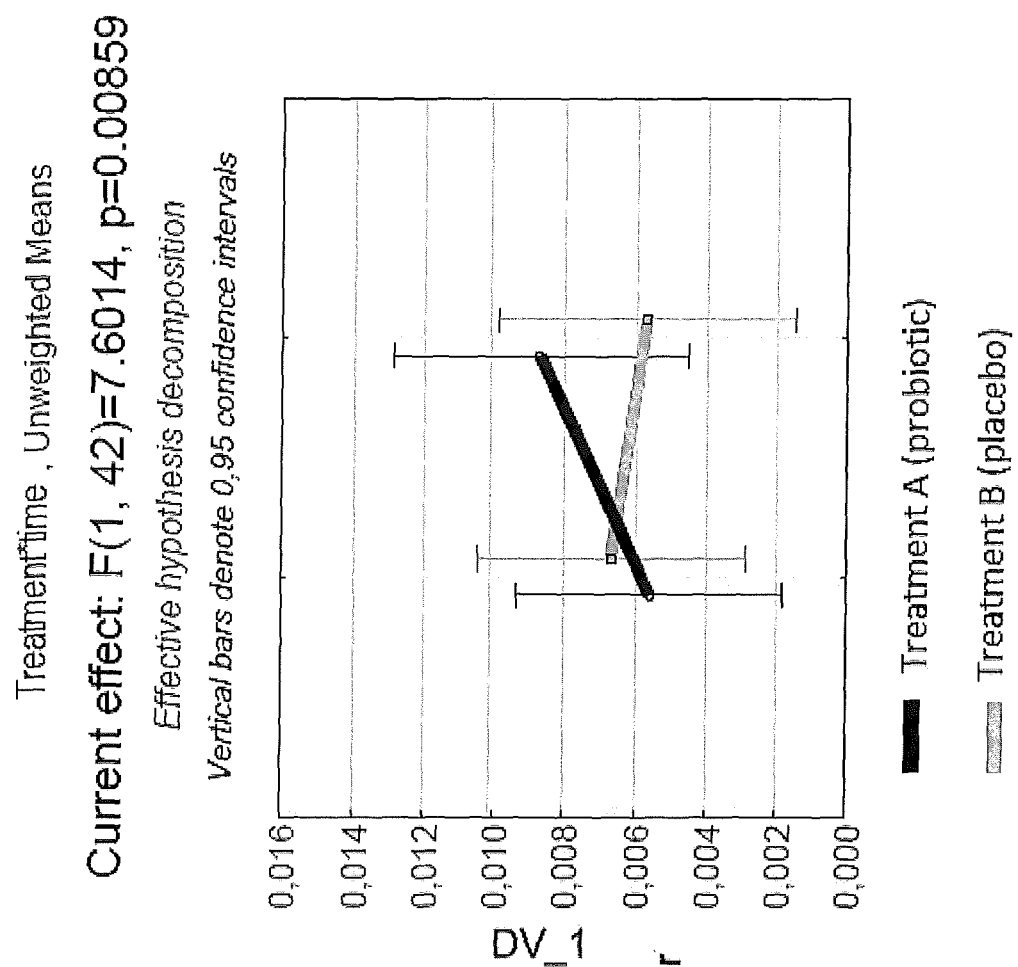
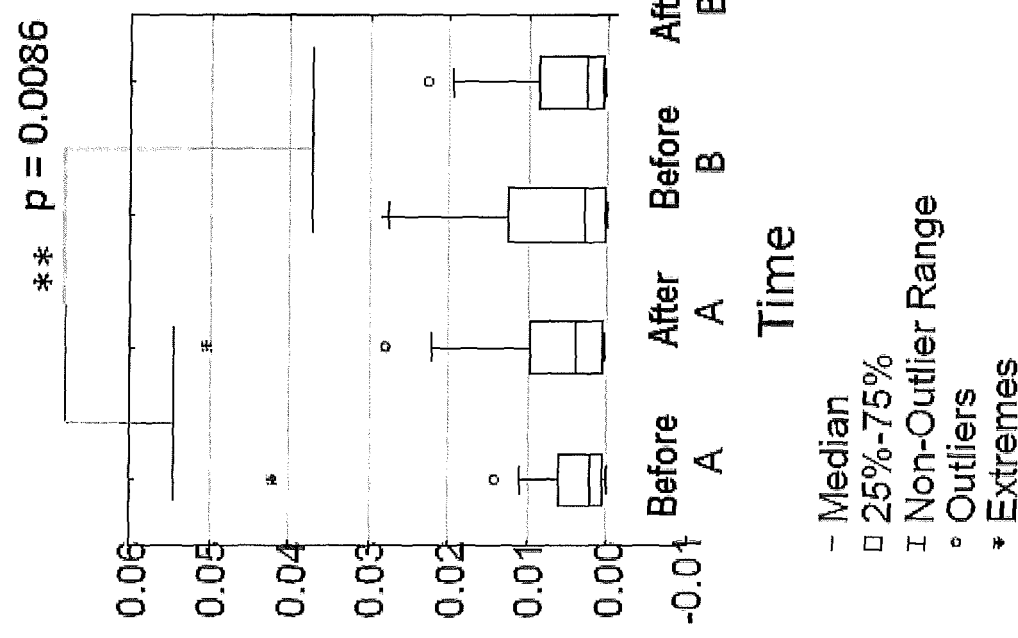
Fig.1.1

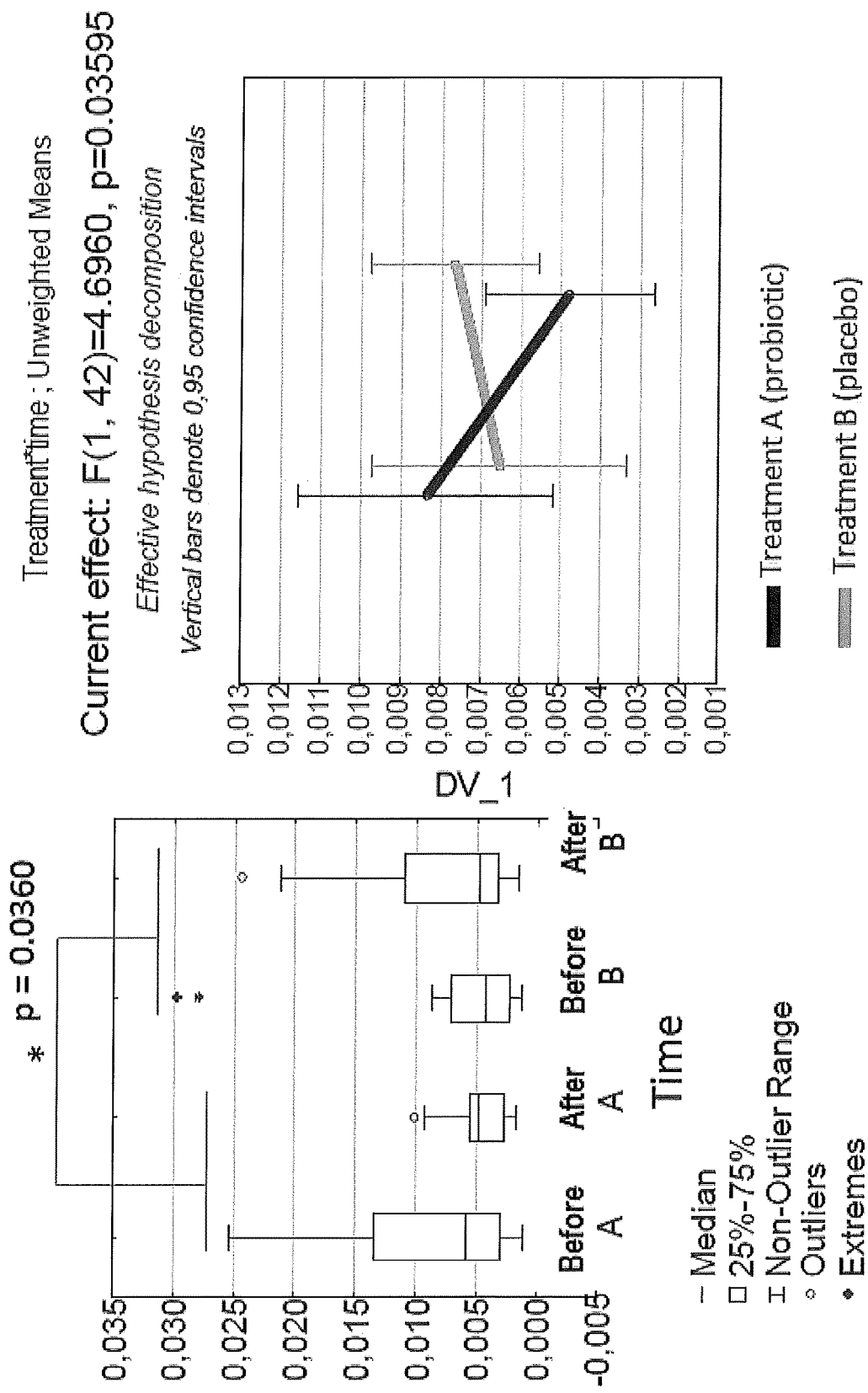
Fig. 1.2

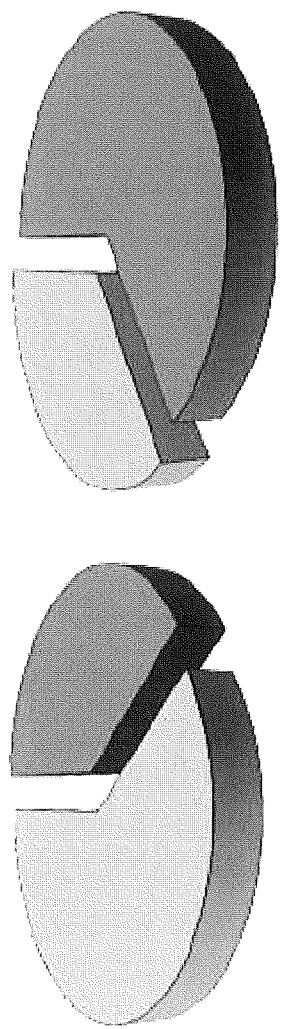
Fig.2.1
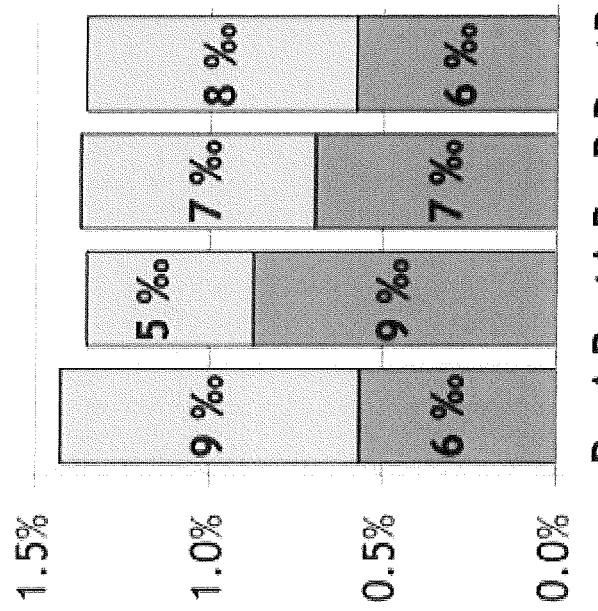
Fig.2.2

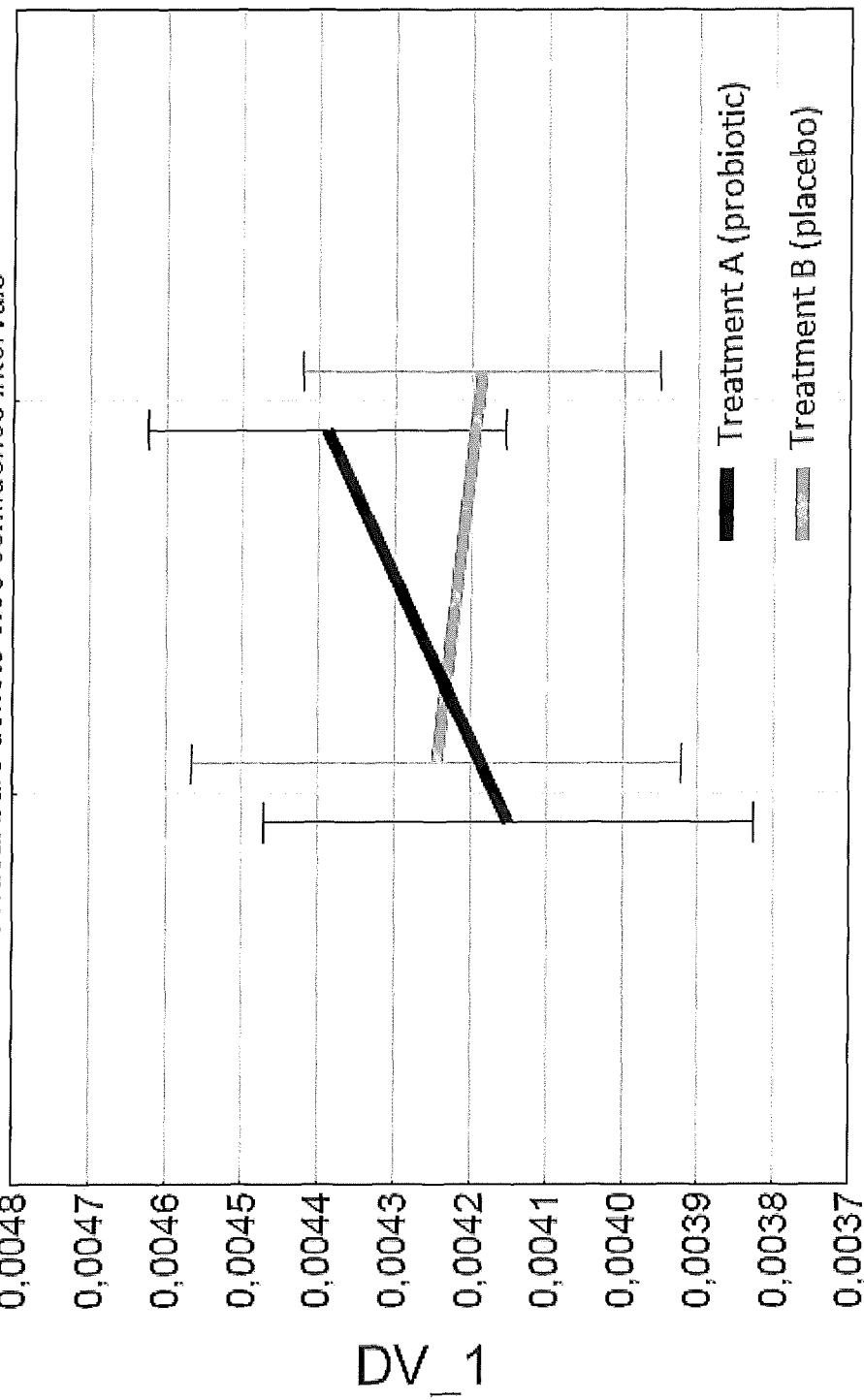

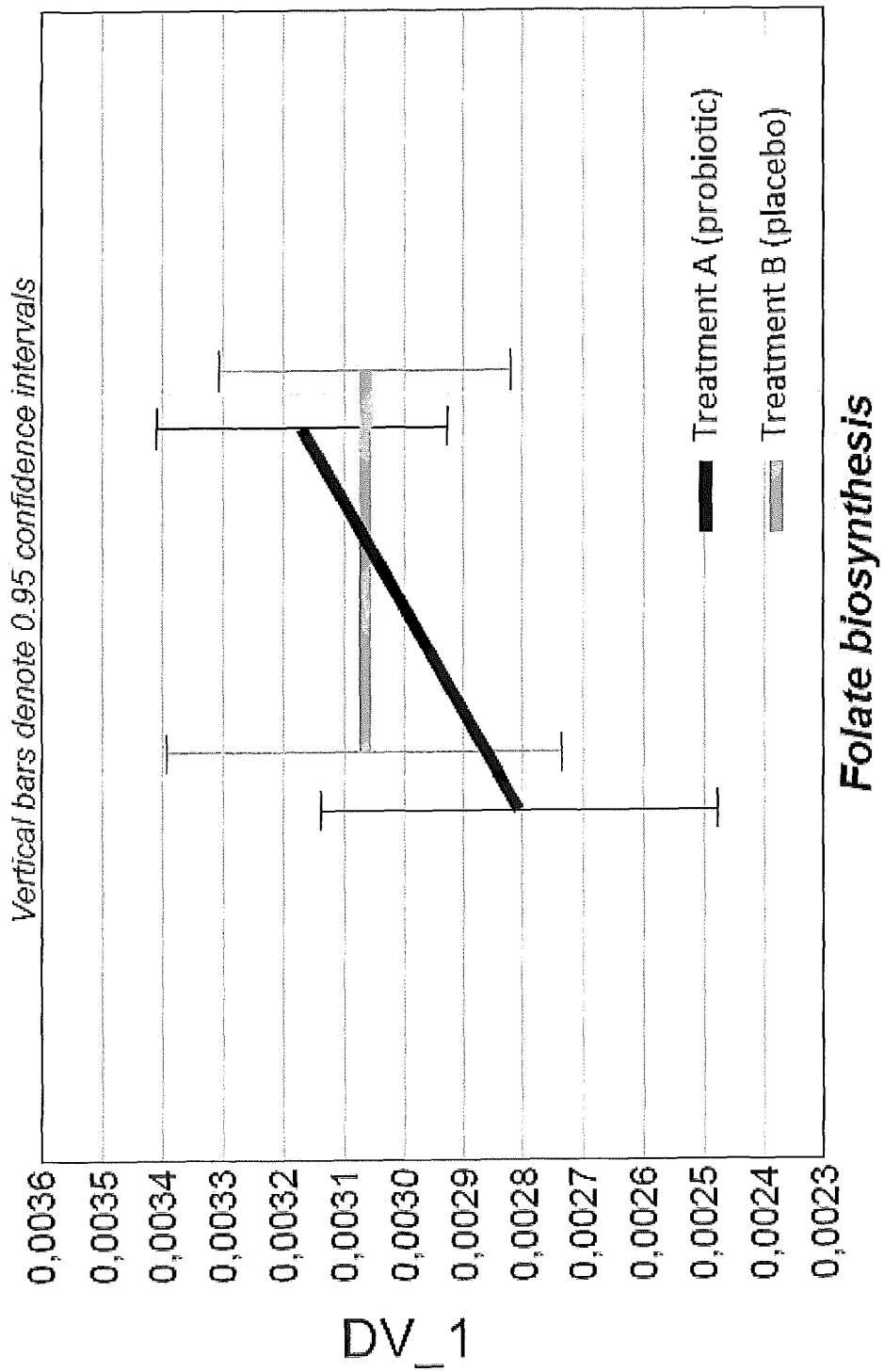

USE OF A COMPOSITION COMPRISING MICROORGANISMS TO INCREASE THE INTESTINAL PRODUCTION OF BUTYRIC ACID, FOLIC ACID OR NIACIN AND/OR DECREASE THE INTESTINAL PRODUCTION OF SUCCINIC ACID

CROSS-REFERENCE TO RELATED APPLICATIONS

This application is a 371 National Stage application of International PCT Application PCT/IB2014/064285, filed Sep. 5, 2014, which claims benefit of priority to Italian Patent Application No. MI2013A001467, filed Sep. 6, 2013, both of which are incorporated herein by reference in their entirety.

The present invention relates to the use of a composition comprising bacteria in order to increase the intestinal production of butyric acid, folic acid or niacin and/or to decrease the intestinal production of succinic acid. Moreover, the present invention relates to the use of said composition for the treatment and/or prevention of an intestinal butyrate- and/or succinate-dependent pathological condition, in particular, for the treatment and/or prevention of intestinal inflammation, diarrhoea, ulcerative colitis or intestinal colopathies.

Intestinal microbiota, also known by the by now obsolete term of intestinal flora, is the whole of the microorganisms, prevalently consisting of bacteria, residing in the intestine and in symbiosis with the body of the host.

The intestinal microbiota is a highly complex ecosystem and the condition of equilibrium among the different microorganisms making up the intestinal is fundamental in order to ensure the body's well-being and health, since the microbiota significantly conditions the development and the homeostasis of the intestinal mucosa of the host individual.

In other words, the intestinal microbiota represents a veritable organ. In fact, qualitative and/or quantitative modifications in the intestinal microbiota of an individual, or so-called disbiosis or dismicrobism, can result in the loss of the intestinal homeostasis, which in turn can condition the etiopathogenesis of a large number of pathologies.

For the purpose of treating a condition of intestinal disbiosis, or, in any case, for the purpose of maintaining the homeostasis of the intestinal microbiota, people often take substances that are defined as probiotics, or, according to the definition of the FAO/WHO, "live microorganisms which, when administered in adequate amounts, confer a health benefit on the host". Similarly, the effectiveness of paraprobiotics for health has also been demonstrated; these are defined as "non-viable microbial cells (intact or broken) or raw cellular extracts which, when administered in adequate amounts (orally or topically), confer a health benefit on the host" (Taverniti and Guglielmetti, 2011).

It is clear that the beneficial activities of a microorganism will vary depending on the composition thereof and, in fact, these are often strain-specific activities.

On the basis of the above considerations, there continues to be a felt need to determine potential new health-promoting and/or therapeutic effects of microorganisms, in particular those included in a probiotic or in a paraprobiotic, in order to broaden the applications of use.

For example, there continues to be a greatly felt need in the art to identify microorganisms capable of modulating the intestinal amount of substances that are particularly beneficial and therapeutic for the body, such as butyric acid, folic acid and nicotinic acid.

Butyric acid is a short-chain fatty acid which is physiologically formed in the colon of humans as a result of the fermentation of dietary fibre by the microbiota.

Butyric acid is the principal source of energy for colon cells (colonocytes) and is therefore a nutrient that is essential for the human body.

At the intestinal level, butyric acid performs various important functions, e.g.: it stimulates the turnover and physiological maturation of colonocytes; it plays a key role in maintaining the integrity of the mucosa and in processes of repairing intestinal lesions; it stimulates the reabsorption of water and sodium in the colon; and it contributes to lowering the intestinal pH, creating an environment that is unfavourable to the development of pathogenic bacteria.

A deficiency of butyric acid can cause inflammatory colitis in humans.

Succinic acid is likewise a short-chain organic acid, of the bicarboxylic type. It is considered ulcerogenic and can cause serious damage to the mucosa. Therefore, an increase in the amount of succinic acid (succinate) is harmful to human health.

Folic acid (vitamin B9, or M or folacin) is a very important vitamin for the whole population, in particular in adults over 50 years of age and in women of a fertile age, because it intervenes (directly or, most of the time, by decreasing the plasma levels of homocysteine) in many vital processes such as DNA synthesis, repair and methylation.

A deficiency of folic acid can lead to macrocytic anaemia, which may be accompanied by leukopaenia and thrombocytopaenia, skin and mucosa alterations and gastrointestinal disorders (malabsorption and diarrhoea).

Niacin (or vitamin PP or vitamin B3), i.e. nicotinic acid and nicotinamide, is important because, among other things, it is the essential component of the coenzymes NAD and NADH and a deficiency thereof causes a pathology known as pellagra. Generally, this pathology begins with problems in the gastrointestinal system, which are then compounded by a photosensitizing dermatitis, mental disorders with fatigue, depression and memory disorders. The present invention responds to the needs of the prior art described above with a composition comprising microorganisms, preferably bacteria of the genus *Lactobacillus* species *paracasei*, capable of (directly and/or indirectly) increasing, in an individual that takes it, the intestinal production of butyric acid, folic acid, niacin and/or salts thereof.

Furthermore, the Applicant has found, wholly unexpectedly, that a composition comprising microorganisms, preferably of the genus *Lactobacillus* species *paracasei*, is capable of (directly and/or indirectly) decreasing the intestinal production of succinic acid and/or salts thereof. Therefore, the composition of the present invention is particularly advantageous for the treatment and/or prevention of intestinal butyrate- and/or succinate-dependent pathological conditions.

Further advantages of the present invention will be more apparent from the detailed description that follows and from the examples which, however, have only a demonstrative, non-limiting purpose.

To enable a better understanding of the detailed description, FIGS. 1-4 have been appended hereto:

FIG. 1.1 shows the result of the statistical analysis demonstrating the increase in the population of bacteria of the genus *Coprococcus* before and after treatment with the composition of the present invention (A) and the decrease thereof, in contrast, before and after treatment with the placebo (B);

FIG. 1.2 shows the result of the statistical analysis demonstrating the decrease in the population of bacteria of the genus *Blautia* before and after treatment with the composition of the present invention (A) and the increase thereof, in contrast, before and after treatment with the placebo (B);

FIG. 2.1 shows the increase in the population of bacteria of the genus *Coprococcus* (dark grey) and the decrease in the population of bacteria of the genus *Blautia* (light grey) before and after treatment with the composition of the present invention;

FIG. 2.2 shows the percentage increase in the population of bacteria of the genus *Coprococcus* (dark grey) and the percentage decrease in the population of bacteria of the genus *Blautia* (light grey) before and after treatment with the composition of the present invention (A) and the percentage decrease in the population of bacteria of the genus *Coprococcus* (dark grey) and the percentage increase in the population of bacteria of the genus *Blautia* (light grey) before and after treatment with the placebo (B);

FIG. 3 shows the result of the statistical analysis which demonstrates the increase in the metabolism of nicotinic acid before and after treatment with the composition of the present invention and the decrease thereof before and after treatment with the placebo;

FIG. 4 shows the result of the statistical analysis which demonstrates the increase in the biosynthesis of folic acid before and after treatment with the composition of the present invention and an absence of any modifications, in contrast, before and after treatment with the placebo.

Figure 5:
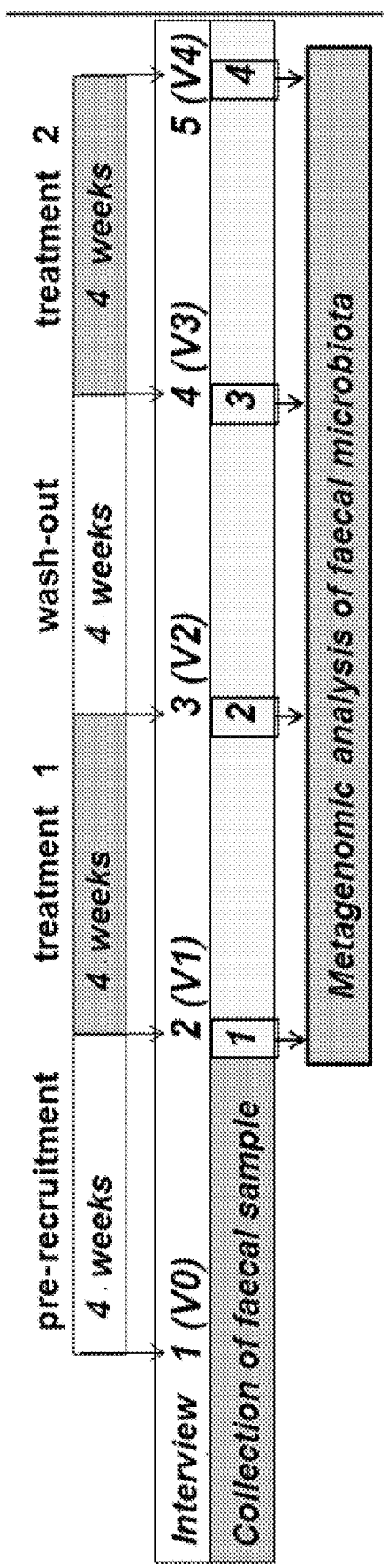
FIG. 5 shows a schematic of the probiotic dietary intervention carried out in accordance with a design crossover.

The present invention relates to the use of a composition comprising microorganisms, preferably at least one bacterium of the genus *Lactobacillus* species *paracasei*, to increase the direct and/or indirect intestinal production of butyric acid and/or salts thereof, and/or folic acid and/or salts thereof, and/or niacin and/or salts thereof and/or to decrease the direct and/or indirect intestinal production of succinic acid and/or salts thereof.

In the context of the present invention, intestinal production means the release, into the environment, of any molecule produced by primary or secondary metabolism by any intestinal microorganism in any region of the intestine.

Moreover, the composition of the present invention can also be used to reduce the intestinal proliferation of pathogenic microorganisms, and/or to promote the integrity of the intestinal mucosa, and/or to promote the processes of repair of intestinal lesions, preferably by increasing the direct and/or indirect intestinal production of butyric acid and/or salts thereof and/or by decreasing the direct and/or indirect intestinal production of succinic acid and/or salts thereof.

Some pathogenic microorganisms particularly sensitive to the composition of the present invention are, for example, enterohaemorrhagic *Escherichia coli*, *Listeria monocytogenes*, *Clostridium difficile*, *Pseudomonas aeruginosa* and *Salmonella* spp.

The above-described uses of the composition of the present invention are intended both for a healthy individual and an individual with a pathological intestinal condition. In particular, in the case of a healthy individual, the composition of the invention performs in that individual, following intake, an action of maintaining the homeostasis of the microbiota and/or of preventing an alteration thereof, and is thus also definable as a probiotic composition (or probiotic).

A further aspect of the present invention relates to the medical use of the composition comprising microorganisms, preferably at least one bacterium of the genus *Lactobacillus* species *paracasei*, for the treatment and/or prevention of an intestinal butyrate- and/or succinate-dependent pathological condition.

In the context of the present invention, intestinal butyrate- and/or succinate-dependent pathological condition means a pathological condition that is sensitive to treatment with butyric acid and/or salts thereof and/or treatment with succinic acid and/or salts thereof. Examples of said pathologies are: diarrhoea, intestinal inflammation, ulcerative colitis, gastric atrophy, intestinal diverticula, stenosis, obstructions and diabetic neuropathy.

In a particularly preferred embodiment of the present invention, the composition comprises the bacterial strain *Lactobacillus paracasei* DG.

The bacterial strain *Lactobacillus paracasei* DG was deposited by SOFAR S.p.A. with the National Collection of Microorganism Cultures of the Pasteur Institute (CNCM) in Paris on May 5, 1995, with the deposit number CNCM 1-1572. CNCM has an address of 25, rue du Docteur Roux 75724 Paris Cedex 15. Initially, the name of the deposited strain was *Lactobacillus casei* DG sub.*casei*.

In a further embodiment of the invention, the direct and/or indirect increase in the intestinal production of butyric acid and/or salts thereof, and/or of folic acid and/or salts thereof, and/or of niacin and/or salts thereof and/or the direct and/or indirect decrease in the intestinal production of succinic acid is ascribable to the intestinal microbiota, preferably bacteria of the genus *Coprococcus* and/or *Blautia*.

In the particularly preferred embodiment of the invention, the direct and/or indirect increase in the intestinal production of butyric acid and/or salts thereof is ascribable to bacteria of the genus *Coprococcus*, and/or the direct and/or indirect decrease in the intestinal production of succinic acid is ascribable to bacteria of the genus *Blautia*.

Therefore, the composition comprising microorganisms, preferably at least one bacterium of the genus *Lactobacillus* species *paracasei*, more preferably the bacterial strain *Lactobacillus paracasei* DG, can also be used to modify the density of the bacterial population of the genus *Coprococcus* and/or *Blautia* in the intestinal microbiota, preferably so as to induce an increase in the bacterial population of the genus *Coprococcus* and/or a decrease in the bacterial population of the genus *Blautia*. In other words, intake of the composition of the present invention modifies the amount of bacteria of the genus *Coprococcus* and/or *Blautia* within the intestinal microbiota. In particular, the bacteria of the genus *Coprococcus* increase and/or the bacteria of the genus *Blautia* decrease following intake of said composition.

The composition used in the present invention comprises said microorganism, preferably said at least one bacterium of the genus *Lactobacillus* species *paracasei*, in live or dead form, as a lysate or extract. In one embodiment of the invention, the composition comprises about 15-billion colony forming units (CFU) of bacteria, preferably 20-25 billion CFU of bacteria.

Preferably, the composition is formulated for oral administration. In particular, the composition is formulated in solid form, preferably in the form of pills, capsules, tablets, granular powder, hard capsules, water-soluble granules, sachets or pellets.

Alternatively, the composition of the invention is formulated in liquid form, for example as a syrup or beverage, or is added to a food, for example to a yogurt, cheese or fruit juice.

Alternatively, the composition of the invention is formulated in a form capable of exerting an action topically, for example as an enema.

In one embodiment of the invention, the composition further comprises excipients generally accepted for the production of probiotic and/or pharmaceutical products.

In a further embodiment of the invention, the composition of the invention can be enriched with vitamins, trace elements such as zinc and selenium, enzymes, prebiotic substances such as fructo-oligosaccharides (FOS), galacto-oligosaccharides (GOS), inulin, guar gum or combinations thereof. Preferably, for the purposes of the uses of the present invention, the composition is taken once a day, more preferably upon awakening.

Alternatively, it can also be taken in the evening, preferably after meals.

EXAMPLE

Treatment.

A randomized, double-blind, placebo-controlled crossover dietary intervention study was conducted on healthy individuals.

Volunteers were recruited in accordance with the following criteria:
- inclusion criteria: healthy men and women, ranging in age between 18 and 55 years who gave their informed consent;
- exclusion criteria: antibiotic treatment in the month preceding the first examination; episodes of viral or bacterial enteritis in the 2 months preceding the first examination; gastric or duodenal ulcers in the 5 years preceding the first examination; pregnancy or breast-feeding; recent or presumed cases of alcoholism and drug intake; other conditions of non-compliance with the study protocol.
- The probiotic dietary intervention was carried out in accordance with a design crossover, as schematized in FIG. 5.

In the pre-enrolment phase (4 weeks) the volunteers followed their usual diet, without consuming probiotic fermented milk products (traditional yogurt was thus permitted), probiotic dietary supplements, or prebiotic dietary supplements.

At the end of the pre-enrolment period, the volunteers were randomized to receive one capsule per day of a probiotic or placebo for 4 weeks.

By way of example, Enterolactis Plus was used as the probiotic to be administered; it consists in 420 mg capsules containing 24 billion CFU (colony forming units) of *Lactobacillus paracasei* strain DG.

The placebo consisted in capsules identical in appearance to the probiotic ones, obviously devoid of the probiotic agent.

The flavour and colour of the active substance (i.e. the probiotic) and the placebo were identical.

The product was taken in the morning on an empty stomach, at least ten minutes before breakfast or, if forgotten, in the evening before going to bed and in any case at least two hours after the last meal.

After the first four weeks of treatment, the volunteers went through a four-week wash-out period identical to the pre-enrolment period.

At the end of the wash-out period, the volunteers took one capsule per day of Enterolactis Plus or placebo for four weeks in accordance with the crossover design described above.

In summary, the study involved 4 phases, each of which lasting 4 weeks:
- Pre-recruitment phase: the individuals underwent neither treatment A nor treatment B.
- Treatment 1: the individuals underwent treatment A or treatment B.
- Wash-out: the individuals underwent neither treatment A nor treatment B
- Treatment 2: the individuals underwent treatment B or treatment A. Treatments A and B can be the composition of the present invention, in the specific example Enterolactis plus, or else the placebo. At the start of the treatment, it was not known what the individual was taking; only at the end of the treatment, when the blind was broken, was the intake sequence known.

Examinations and Sample Collection.

Each volunteer was initially instructed as to the entire procedure to be followed, which involved a total of 5 meetings per volunteer.

During the first meeting, informed consent was obtained along with the volunteer's personal data. The volunteer also received general information about how the study was to be carried out and was instructed about the changes in the diet to be applied in the subsequent 4 weeks of pre-enrolment (prohibition from consuming the previously specified products).

After 4 weeks, the volunteer went to the second meeting with a faecal sample (sample T0), collected during the previous 24 hours in a special container handed over during the first meeting.

To ensure optimal preservation, the faecal samples were stored at room temperature and delivered to the laboratory within 24 hours.

During the second meeting, moreover, the volunteer was given the probiotic product (or placebo) to be taken during the next 4 weeks. Moreover, the volunteer was instructed as to how to take the product.

At the end of the 4 weeks of taking the product (or placebo), the volunteer went to the third meeting with another faecal sample (sample T1) collected during the previous 24 hours.

During the third meeting, the volunteer completed a questionnaire on the possible effects, both positive and undesirable ones, deriving from consumption of the product.

The volunteer was then instructed about the next 4 weeks, during which he or she again did not take the previously mentioned products.

At the end of these 4 weeks, the volunteer went to the fourth meeting with a faecal sample (sample T2) and received the probiotic product (or placebo) to be taken during the next 4 weeks.

Finally, after 4 weeks of taking the product (or placebo), the volunteer went to the fifth meeting to deliver the last faecal sample (sample T3).

During this last meeting, the volunteer has completed a questionnaire analogous to the one received during the third meeting.

All the faecal samples collected were stored at −20° C. for no more than 7 days before being subjected to analysis of the microbiota.

Analysis of Faecal Microbiota

The faecal microbiota was evaluated by analyzing the nucleotide sequence of portions of the gene encoding the 16S rRNA bacterial ribosomal subunit. More specifically, a metagenomic strategy was adopted; it consists in short in the following steps:

1. extracting, quantifying and normalizing the metagenomic DNA from the faecal samples;
2. amplifying the V3 hypervariable region of the bacterial gene encoding the 16S rRNA by PCR;
3. quantifying the PCR products;
4. sequencing the amplification products;
5. bioinformatically analyzing the sequences.

The procedures according to steps 1 and 3 are techniques that are well known in the art and they are thus performed with the protocols commonly used in this field. For example, the methods described in laboratory manuals such as those by Sambrook et al. 2001, or Ausubel et al. 1994.

Step 2 of amplifying the V3 region of the 16S ribosomal RNA genes was performed by means of the DNA amplification technique known as PCR, using Probio_Uni 5'-CCTACGGGRSGCAGCAG-3' (SEQ ID NO: 1) and Probio_Rev 5'-ATTACCGCGGCTGCT-3' (SEQ ID NO: 2) as oligonucleotides (primers).

In particular, the pair of primers SEQ ID NO: 1 and 2 2 amplifies the V3 region of the 16S rRNA gene.

Step 4 can be performed with the techniques known in the art for this purpose, for example techniques based on the Sanger method, pyrosequencing or the Ion Torrent Fusion Primers sequencing method used in the specific example of the present invention according to the protocol described in the materials and methods section of the scientific article by Milani et al. (2013).

In the case of the Ion Torrent technique, the primers are designed and synthesized in such a way as to include, at the 5' end, one of the two adaptor sequences used in this specific DNA sequencing technique. In this case, the adaptor sequences were SEQ ID NO: 1 and 2.

The conditions under which the PCR was performed are the following:
  5 minutes at 95° C.;
  30 seconds at 94° C., 30 seconds at 55° C., and 90 seconds at 72° C. for 35 cycles;
  10 minutes at 72° C.

At the end of the PCR, the integrity of the amplificate was verified by electrophoresis.

Step 5 of the method, necessary for characterizing the microbial communities, can be carried out with numerous techniques presently known for this purpose. More specifically, use was made of: hierarchical clustering, taxonomic analysis and construction of phylogenetic dendrograms with heat maps according to the protocol described in the materials and methods section of the scientific article by Milani et al. (2013); more specifically, the analysis of sequence data was conducted using QIIME software.

Statistical Analysis of the Data

The statistical analysis was conducted using STATISTICA software (Statsoft Inc., Tulsa, OK, USA).

In order to reveal significant differences, the data were analyzed using both parametric (multivariate and univariate repeated-measures ANOVA) and non-parametric (Wald-Wolfowitz and Mann-Whitney) statistical methods.

The normality of the data series (important assumption for ANOVA) was evaluated by means of the Shapiro-Wilk and Kolmogorov-Smirnov tests.

Results of the Treatment

The study was completed by a total of 22 individuals (11 females and 11 males).

Thirty-three individuals were initially enrolled, but 11 of them withdrew early for various reasons: intake of antibiotics (4), refusal to continue the study (1), frequent episodes of diarrhoea (1), intake of other probiotics during the study period (3), drastic change in eating habits (1), and seasonal influenza with episodes of diarrhoea (1).

Upon the conclusion of the study and completion of the analysis of the results of the two treatments, the blind was broken and it was seen that: treatment A is the active treatment, containing *Lactobacillus paracasei* DG; treatment B is the placebo, identical on the exterior to the active treatment, but devoid of lactobacilli.

When the data obtained from the study were analyzed, a high stability, from a taxonomic viewpoint, of the intestinal microbiota of the study participants was observed.

In fact, it was found that:
  Two bacterial divisions of the 15 identified, namely, Bacteroidetes and Firmicutes, constitute over 90% of the sequences;
  11 families of the 131 identified constitute over 90% of the sequences; and
  20 genera of the 262 identified constitute over 90% of the sequences. Moreover, this study confirmed that human intestinal microbiota at lower taxonomic levels (i.e. at the family and genus levels) is highly variable from one individual to another.

Therefore, the experimental evidence demonstrated the necessity of conducting, on a healthy population, crossover intervention trials in order to prevent the marked interindividual variability from hiding the possible effects of the probiotic treatment or leading to false statistical positives.

When the modifications induced in the intestinal microbiota by the two treatments were evaluated, a statistically significant difference emerged in terms of genera only in the group receiving the treatment with *Lactobacillus paracasei* DG (active treatment). More specifically, an increase in the genus *Coprococcus* was observed. In fact, as can be noted in FIGS. 1.1, 2.1 and 2.2, before and after treatment with *Lactobacillus paracasei* DG a statistically significant increase in coprococci was observed. In contrast, a moderate reduction thereof was seen in the group receiving the placebo treatment.

Moreover, after treatment with *Lactobacillus paracasei* DG, a statistically significant reduction in bacteria of the genus *Blautia* was observed. In contrast, a slight increase thereof was observed in the group receiving the placebo treatment (FIGS. 1.2, 2.1 and 2.2)

Coprococci are among the main producers of butyrate at the intestinal level. Butyrate is a fundamental compound at the intestinal level, since on the one hand it contributes to restoring the functional integrity of the intestinal mucosa and maintaining it over time, and on the other hand it has important anti-inflammatory effects, so much so that it is used as an adjuvant to dietary treatments for intestinal colopathies (e.g. chronic inflammatory intestinal diseases).

Moreover, an analysis of their genome reveals that these bacteria can use succinate as a fermentation substrate.

This information is fundamental, in consideration of the fact that members of the genus *Blautia* generate acetate and succinate as main end products of the fermentation of glucose.

Succinate is considered an ulcerogenic factor, capable, therefore, of exacerbating the condition of individuals with ulcerative colitis, since it is probably to blame for the mucosal damage present above all in the active phases of the disease.

In conclusion, following treatment with a probiotic, in this case following the administration of *Lactobacillus paracasei* DG, one observes an increase in the bacteria belonging to the genus *Coprococcus* and hence an increase in the intestinal concentration of butyrate.

At the same time, one observes a reduction in the concentration of succinate, which may be to blame for mucosal damage in individuals with ulcerative colitis, in a direct manner, because following treatment with the probiotic, in this case following the administration of *Lactobacillus paracasei* DG, there is a reduction in the bacteria belonging to the genus *Blautia*, and, in an indirect manner, because the increased population of coprococci is further able to decrease the concentration of succinate by using it as a substrate in their fermentation process.

In conclusion, following treatment with the probiotic, in the specific example following the administration of *Lactobacillus paracasei* DG, there is an increase in the concentration of butyric acid in the faeces of individuals, with a simultaneous reduction in other organic acids, such as succinic acid.

The data relating to the composition of faecal microbiota were used, finally, in a bioinformatic analysis aimed at a virtual reconstruction of the metagenome based on knowledge of the bacterial genomes (Okuda S, Tsuchiya Y, Kiriyama C, Itoh M, Morisaki H. Virtual metagenome reconstruction from 16S rRNA gene sequences. Nat Commun. 10 2012; 3:1203); in other words it was established in silico which potential genes are present and how abundantly in a given microbiota. This analysis made it possible to verify a putative increase in the encoding genes for the synthesis of folic acid and metabolism of nicotinic acid (FIGS. 3 and 4). These two molecules represent important vitamins for the human host (respectively named vitamin B9 and B3). Vitamin B9, in particular, represents a nutritional factor of primary importance, a deficiency of which, especially in specific physiological conditions such as pregnancy, can lead to serious health consequences. Treatment with the probiotic used in this study could therefore favor the ability of intestinal microbiota to produce folic 20 acid (vitamin B9), with a consequent nutritional benefit for the human host.

orally administering to the healthy subject, a composition comprising a bacterium *Lactobacillus paracasei* DG, Accession Number CNCM 1-1572, in 15-30 billion colony forming units (CFU), to prevent in the healthy subject the intestinal butyrate and succinate-dependent pathological condition, wherein said intestinal pathological condition is diarrhoea and at least one of gastric atrophy, intestinal stenosis, intestinal obstructions and diabetic neuropathy.

2. The method according to claim 1, wherein said bacterium *Lactobacillus paracasei* DG is a live or a dead bacterium, or a bacterial lysate or extract.

3. The method according to claim 1, wherein said composition is administered orally in the form of pills, capsules, tablets, granular powder, hard capsules, water-soluble granules, sachets or pellets.

4. The method according to claim 1, wherein said composition further comprises dietary fibres having prebiotic activity.

5. The method of claim 1, wherein the intestinal pathological condition is diarrhoea associated with gastric atrophy.

6. The method of claim 1, wherein the intestinal pathological condition is diarrhoea associated with stenosis.

7. The method of claim 1, wherein the intestinal pathological condition is diarrhoea associated with obstructions.

8. The method of claim 1, wherein the intestinal pathological condition is diarrhoea associated with diabetic neuropathy.

9. The method according to claim 4, wherein said composition further comprises vitamins, trace elements and/or enzymes.

---

---

The invention claimed is:

1. A method for preventing an intestinal butyrate and succinate-dependent pathological condition in a healthy subject, comprising

10. The method according to claim 4, wherein the dietary fibres having prebiotic activity comprise inulin and/or guar gum.

\* \* \* \* \*

SEQUENCE LISTING

<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: Synthesized

<400> SEQUENCE: 1
cctacgggrs gcagcag                                                17

<210> SEQ ID NO 2
<211> LENGTH: 15
<212> TYPE: DNA
<213> ORGANISM: Artificial Sequence
<220> FEATURE:
<223> OTHER INFORMATION: Synthesized

<400> SEQUENCE: 2
attaccgcgg ctgct                                                  15